United States Patent

Katakami et al.

Patent Number: 5,114,941
Date of Patent: May 19, 1992

[54] PYRIMIDINEDIONE DERIVATIVE COMPOUNDS, METHOD FOR PREPARING SAME, AND ANTIARRYTHMIC AGENTS CONTAINING SAME

[75] Inventors: Tsutomu Katakami; Tatsuro Yokoyama; Haruki Mori; Nobuya Kawauchi; Joji Kamiya; Masaaki Ishii, all of Mobara, Japan

[73] Assignee: Mitsui Toatsu Chemicals, Incorporated, Tokyo, Japan

[21] Appl. No.: 618,245

[22] Filed: Nov. 27, 1990

[30] Foreign Application Priority Data

Dec. 1, 1989 [JP] Japan .................. 1-310615

[51] Int. Cl.$^5$ ............... A61K 31/495; A61K 31/505; C07D 405/12
[52] U.S. Cl. .................... 514/253; 544/295; 544/310
[58] Field of Search ............... 544/295, 310; 514/253

[56] References Cited

U.S. PATENT DOCUMENTS 4,216,314 8/1980 Raabe et al. .................. 544/310
5,008,267 4/1991 Katakami et al. .................. 544/310

FOREIGN PATENT DOCUMENTS 352613 1/1990 European Pat. Off. .

OTHER PUBLICATIONS

E. M. Vaughan Williams, "Advances in drug research" 1974, pp. 69–101.

Primary Examiner—Cecilia Shen
Attorney, Agent, or Firm—Nixon & Vanderhye

[57] ABSTRACT

A pyrimidinedione derivative compound has a basic backbone in which a 4-oxobenzopyran ring group part and a pyrimidinedione part are linked by a structure comprising an alkyl chain containing at least two nitrogen atoms and one oxygen. The pyrimidinedione derivative is useful for a medical treatment of cardiac arrhythmias.

5 Claims, No Drawings

PYRIMIDINEDIONE DERIVATIVE COMPOUNDS, METHOD FOR PREPARING SAME, AND ANTIARRYTHMIC AGENTS CONTAINING SAME

BACKGROUND OF THE INVENTION (i) Field of the Invention

The present invention relate to novel pyrimidinedione derivatives and acid addition salts thereof, to methods of preparing the same and to pharmaceutical agents containing the same, which are effective for the treatment of cardiac dysfunctions such as arrhythmia and cardiac insufficiency.

(ii) Description of the Related Art

The mechanism of the occurrence of arrhythmia is complicated. Abnormalities in stimulation production and disorders in the conducting system or combinations thereof are considered to be responsible.

As to disorders in excitation conduction, the reentry theory is representative.

One of the conditions of occurrence of arrhythmia is irregularity in the refractory period in various parts of the heart. In addition, one-directional block, shortened refractory period, delay in conduction, the presence of circus movement are complicatedly involved Heretofore, various antiarrythmic agents have been used for the treatment of arrhythmia.

The antiarrythmic agents are classified into four groups according to their modes of action.

That is, E. M. Vaughan Williams (Vaughan Williams E. M.; "Advances in drug research, Vol. 9", ed. by Harper N. J., Simmonds A. B., Academic Press, London, 1974, pages 69–101) have classified the antiarrythmic agents into the following four groups in accordance with their actions against the action potential of cardiac muscle or against the ionic current which generates the action potential. Class I: Sodium channel depressors These agents are efficacious in repressing a sodium current. However, these agents have no or only minute effects on the retention time of the normal action potential and decrease the maximum rising velocity ($V_{max}$) of the sodium current. The antiarrythmic agents which belong to this class have a high antiarrythmic activity but at the same time strongly repress cardiac functions. Careful consideration is required in administering to patients with cardiac failure or hypotension Class II: Beta-blocking agents The agents in this class, represented by propranolol, are efficacious in the beta-blocking action and are useful in treating patients with arrhythmia in which the sympathetic nerve is involved. However, the care must be taken for use since these agents have side-effects caused by the beta-blocking action, such as depression of cardiac functions, induction of bronchial asthmatic attack and hypoglycemic seizures Class III: Pharmaceutical agents for prolonging the retention time of the action current.

These agents are efficacious in remarkably prolonging the retention time of the action current of the cardiac muscle and in prolonging an effective refractory period. Re-entry arrhythmia is considered to be suppressed by the action of the pharmaceutical agents of Class III. The medicaments of this Class III include aminodarone and bretylium However, all the agents have severe side effects, and therefore, careful consideration is required for use. Class IV: Calcium antagonists These agents control a calcium channel and suppress arrhythmia due to automatic sthenia of sinoatrial nodes and to ventricular tachycardia in which atrial nodes are contained in the re-entry cycle.

Among these antiarrythmic agents, pharmaceutical agents of the Class III type are considered to be particularly important and most efficacious, and known to be effective on ventricular arrhythmia which is most fatal.

SUMMARY OF THE INVENTION

Various medicinal agents have already been developed and used as antiarrythmic agents.

Search for ideal antiarrythmic agents has been pursued for treatment of arrythmia which has complicated generating mechanisms and requires administration of such agents for a long period of time However, satisfactory results have not been achieved so far.

The present invention has been accomplished in view of the present situation regarding antiarrythmic agents. Thus, an object of the present invention is to provide a novel compound which is useful as a Class III type antiarrythmic agent and to provide a process for producing the same.

Another object of the present invention is to provide a novel compound which is effective in improving cardiac dysfunction such as cardiac insufficiency and a process for the preparation of the same.

Still another object of the present invention is to provide a pharmaceutical agent, which contains the novel compound as an effective component, for the treatment of cardiac dysfunctions such as arrythmic and cardiac insufficiency.

In the course of the intensive study to solve the above-mentioned problems, the present inventors have found compounds of the formula (1) shown below and acid addition salts thereof. Furthermore, they have investigated the pharmacological properties of these compounds, and as a result, they have found that these compounds have pharmacological characteristics for markedly prolonging the retention time of the action potential of cardiomuscular cells and for markedly prolonging the ventricular refractory period in animal experiments using adult dogs. In consequence, the present invention has been achieved on the basis of the above-mentioned knowledge.

Furthermore, the present inventors have found that the compounds of the present invention have a positive inotropic action and are useful as therapeutic agents for cardiac insufficiency.

The compounds of the present invention can be utilized to provide antiarrythmic agents and therapeutic agents for cardiac insufficiency.

DETAILED DESCRIPTION OF THE PREFERRED EMBODIMENTS

The compounds of the present invention include compounds represented by the formula (1)

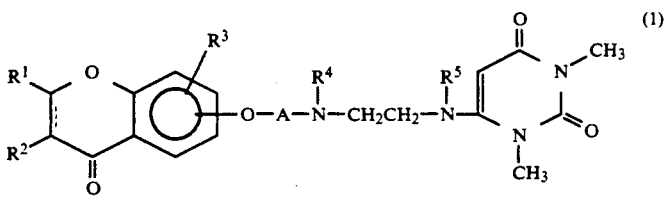

and acid addition salts thereof, and more specifically, these compounds are mentioned in examples which will be described hereinafter.

In this formula (1), A is $-(CH_2)_n-$ (n is 2 or 3) or $-CH_2CH(OH)CH_2-$, and $R^1$ is hydrogen, a lower alkyl group, lower alkoxycarbonyl group, phenyl group, 4-pyridyl group, 3-pyridyl group or 2-pyridyl group, $R^2$ is hydrogen, a lower alkyl group or phenyl group, $R^3$ is hydrogen or a nitro group, $=$ is a single bond or double bond, $R^4$ is a lower alkyl group which may be substituted by a hydroxyl group, and $R^5$ is hydrogen or may be combined with $R^4$ to form $-CH_2CH_2-$.

In the compound of the above-mentioned formula (1), examples of the lower alkyl groups represented by $R^1$ and $R^2$ include alkyl groups having 1 to 3 carbon atoms such as a methyl group, ethyl group, propyl group and isopropyl group. Examples of the lower alkoxycarbonyl group represented by $R^1$ include a methoxycarbonyl group, ethoxycarbonyl group, propoxycarbonyl group and isopropoxycarbonyl group.

Furthermore, examples of the lower alkyl group represented by $R^4$ include alkyl groups having 1 to 3 carbon atoms such as a methyl group, ethyl group, propyl group and isopropyl group, and examples of the hydroxyl group-substituted lower alkyl group represented by $R^4$ include a 2-hydroxyethyl group, 3-hydroxypropyl group and 2-hydroxypropyl group.

$R^3$ is preferably present at the 6-position or 8-position of the 1-benzopyran ring in the above-mentioned formula (1).

In addition, the substituent represented by the formula (2)

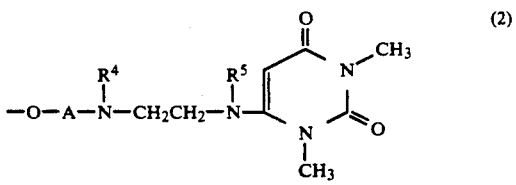

[wherein A, $R^4$ and $R^5$ are defined as in the formula (1)] is preferably present at the 5-position or 6-position of the 1-benzopyran ring in the above-mentioned formula (1).

The expression "pharmaceutically acceptable" used to describe the pharmaceutically acceptable acid addition salts in the compounds of the above-mentioned formula (1) means that remarkable side effects or toxicity does not appear and that its pharmaceutical activities are not extinguished, when administered to men. These acid addition salts can be produced by neutralization of the corresponding free bases.

Examples of the acids from which these pharmaceutically acceptable salts can be prepared include organic acids and inorganic acids, such as hydrochloric acid, hydrobromic acid, phosphoric acid, sulfuric acid, nitric acid, methanesulfonic acid, maleic acid, oxalic acid, malonic acid, succinic acid, fumaric acid, tartaric acid, citric acid, lactic acid and benzenesulfonic acid.

When the compounds shown by the above-mentioned formula (1) were applied to the following arrhythmia pathological models, all the compounds demonstrated efficacy.

Atrial fibrillation model

Atrial fibrillation model animals were made in accordance with the method of A. L. Goldberger et al. (International Journal of Cardiology, Vol. 13, p. 47-55, 1986) by anesthetizing adult mongrel dogs with pentobarbital sodium (30 mg/kg, intravenous administration). Using these atrial fibrillation model animals, the effects of the compounds of the present invention on the atrial fibrillation model were investigated by administering the compounds intravenously at a dose of 0.1-10 mg/kg. As a result, it was confirmed that all the compounds of the present invention had therapeutic effects on atrial fibrillation.

Ventricular tachycardia model

Adult mongrel dogs were anesthetized with pentobarbital sodium (30 mg/kg, intravenous administration). A left thoracotomy was performed in the fourth intercostal space under artificial respiration, and the left anterior descending coronary artery was ligated at the border of the atrial appendage. The blood was then recirculated 120 minutes after the ligation, so that a cardiac infarction lesion was formed to readily induce tachycardia in each animal.

Thereafter, the ventricular tachycardia model animals were made by inducing ventricular tachycardia in accordance with the method of Lynch (Journal of Cardiovascular Pharmacology, Vol. 6, p. 1132-1141, 1984). Using these model animals, it was confirmed that the eompounds of the present invention had therapeutic effects on ventricular tachycardia when administered intravenously at a dose of 0.1 to 3 mg/kg.

As understood from the foregoing, the compounds of the present invention have effective therapeutic effects on the arrhythmia pathology model, i.e., atrial fibrillation model and ventricular tachycardia model, thus they are useful for the treatment and prevention of arrhythmia.

Furthermore, the effects of the compounds of the present invention on cardiac functions were investigated, so that the following results were obtained.

Mongrel dogs (body weights: 8-15 kg) were anesthetized with pentobarbital sodium (30 mg/kg, intravenous administration). A microsensor catheter was then inserted through the common carotid artery into the left ventricle of each animal so that primary differential values (dp/dt) of the inner pressure of the left ventricle and electrocardiograms were recorded. The compounds of the present invention were administered intravenously to the dogs (1 mg/kg) and changes in the dp/dt and electrocardiograms were investigated.

As a result, it was revealed that the compounds of the present invention significantly increased the values of dp/dt max and significantly extended QTc on the electrocardiograms.

Consequently, it was confirmed that the compounds of the present invention had an antiarrythmic action and particularly were useful as Class III type antiarrythmic agents. Furthermore, the significant increase in dp/dt max demonstrated that the compounds of the present invention had a positive inotropic action and accordingly they were useful as therapeutic agents for cardiac insufficiency.

As mentioned above, in general, most of patients with arrhythmia have deficiency in cardiac functions. In the case where, for example, antiarrythmic agents classified in Class I or II are given to such patients, the greatest care has to be taken for use because these agents exert more or less antiarrythmic action as well as a negative inotropic action (action to further repress cardiac functions) (Eivind S. Platous, Journal of Cardiovascular Pharmacology, Vol. 8, No. 3, p. 459, 1986).

On the contrary, as mentioned above, the compounds of the present invention have a positive inotropic action to significantly increase the dp/dt max, as well as an antiarrythmic action. Accordingly, it can be expected that these compounds provide satisfactory results to the arrhythmia patients whose cardiac functions are depressed.

Representative examples of processes for the production of the compounds of the formula (1) of the present invention will be described hereinafter, but the present invention should not be limited to these examples.

Of the compounds having the above-mentioned formula (1), a compound represented by the formula (5)

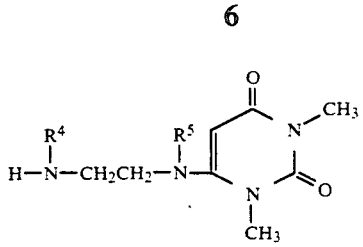

(4)

[wherein $R^4$ and $R^5$ are defined as in the above-mentioned formula (1)] without using any solvent, or alternatively they are dissolved or suspended in a suitable solvent or dispersant, and reaction is then carried out, whereby the compound of the formula (5) can be obtained.

Examples of the substituent which can become the leaving group in the formula (3) include an allylsufonyloxy group such as a paratoluenesulfonyloxy group, and an alkylsulfonyloxy group such as a methanesulfonyloxy group.

This reaction is effected at a temperature in the range of from room temperature to the reflux temperature of the reaction mixture, and for example, it can be selected from the range of from 20° to 150° C.

Furthermore, the reaction can be allowed to preferably proceed by adding a base to the reaction solution.

The suitable solvent or dispersant used in the reaction can be optionally selected, so long as it is inactive to the reaction solution. Examples of the usable solvent and dispersant include alcohols such as methanol and ethanol, tetrahydrofuran, dimethylformamide, chloroform, dichloromethane, dioxane, benzene and dimethyl sulfoxide.

In addition, examples of the base having the effect of the reaction acceleration include triethylamine, pyridine, potassium carbonate, sodium carbonate and so-

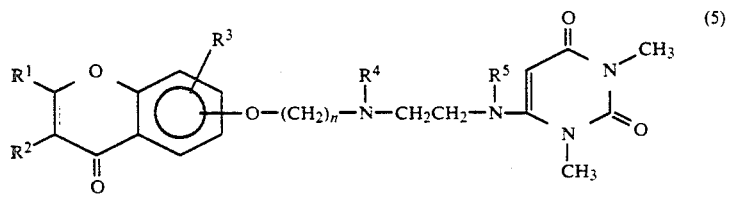

(5)

[wherein $R^1$, $R^2$, $R^3$, $R^4$, $R^5$ and $=$ are defined as in the aforesaid formula (1), and n is 2 or 3] can be prepared by a process containing the following step (a):

Step (a)

A compound represented by the formula (3)

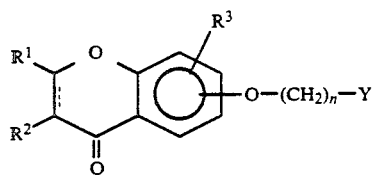

(3)

[wherein $R^1$, $R^2$, $R^3$ and $=$ are defined as in the aforesaid formula (1), n is 2 or 3, and Y is a halogen atom or a substituent which can become a leaving group when reacted with a compound of the following formula (4)] is mixed with the compound represented by the formula (4)

dium hydroxide.

The compound of the formula (4) used in the above step (a) in which $R^4$ and $R^5$ are not linked to each other can be prepared by a process containing the following step (b):

Step (b)

A compound represented by the formula (10)

$H_2H-R^4$ (10)

[wherein $R^4$ is defined as in the above-mentioned formula (1)] is mixed with a compound represented by the formula (11)

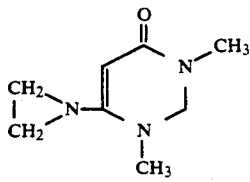
(11)

without using any solvent, or alternatively they are dissolved or suspended in a suitable solvent or dispersant, and reaction is then carried out, whereby the compound of the formula (4) in which $R^4$ and $R^5$ are not linked to each other can be obtained.

This reaction is effected at a temperature in the range of from room temperature to the reflux temperature of the reaction mixture, and for example, it can be selected from the range of from 30° to 170° C.

Furthermore, the reaction can be allowed to preferably proceed by adding an acid catalyst to the reaction solution.

The suitable solvent or dispersant used in the reaction can be optionally selected, so long as it is inactive to the reaction solution. Examples of the usable solvent and dispersant include what have been enumerated in the preceding paragraph regarding the step (a).

In addition, examples of the above-mentioned acid catalyst include p-toluenesulfonic acid and acidic ion exchange resins [e.g., trade name Umberlist such as Umberlist 15 made by Rohm & Hass Co., in U.S.A.].

The compound of the formula, (11) used in the above-mentioned step (b) can also be prepared by a process containing the following step (c):

Step (c)

A compound represented by the formula (12)

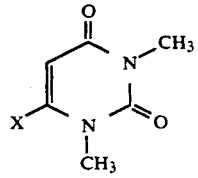
(12)

[wherein X is a halogen atom] is reacted with 2-aminoethanol in the same manner as in the aforesaid step (a) in order to produce a compound having the following formula (13):

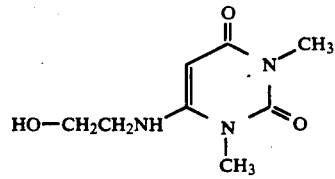
(13)

Next, this compound of the formula (13) is sulfonated with methanesulfonyl chloride, p-toluenesulfonyl chloride or the like, or alternatively the compound of the formula (13) is reacted with thionyl chloride, potassium tribromide or the like to form a halide, and then this sulfonated compound or halide is then stirred at room temperature or under heating in the presence of sodium hydride, potassium carbonate or sodium hydroxide in a solvent such as dimethyl sulfoxide or methanol, whereby the compound of the formula (11) can be obtained.

Furthermore, the compound having the formula (5) can also be prepared by a process containing the following step (d):

Step (d)

A compound represented by the formula (6)

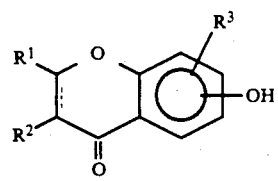
(6)

[wherein $R^1$, $R^2$, $R^3$ and ≐ are defined as in the aforesaid formula (1)] is reacted with a compound having the formula (7)

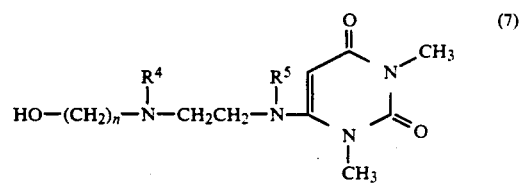
(7)

[wherein $R^4$ and $R^5$ are defined as in the above-mentioned formula (1), and n is 2 or 3] in the presence of a dehydration/condensation agent, and at the time of this reaction, both the compounds are dissolved or suspended in a suitable solvent or dispersant (the application of the Mitunobu's reaction; O. Mitunobu, Synthesis, pages 1–28, 1981), whereby the compound of the formula (2) can be obtained.

The reaction is carried out at a reflux temperature of the solvent or dispersant or less, and for example, the reaction temperature is selected from the range of from −10° to 80° C.

As the dehydration/condensation agents which can be used in the reaction, various kinds of dehydration/condensation agents can be utilized which are usually used for the formation of an ether bond, and above all, a mixed condensation agent of diethyl azodicarboxylate and triphenylphosphine is preferable.

As the suitable solvent or dispersant used in the reaction, any one can be used without restriction, so long as it is inactive to the reaction solution. Examples of the solvent and dispersant include tetrahydrofuran, dimethylformamide, chloroform, dichloromethane and dioxane.

The compound of the above-mentioned formula (7) can be prepared by a process containing the following step (e):

Step (e)

A compound represented by the formula (14)

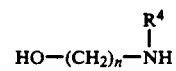
(14)

[wherein $R^4$ is defined as in the above-mentioned formula (1), and n is 2 or 3] is reacted with the above-mentioned compound (11) in the same manner as in the preceding step (b), thereby obtaining the compound of the formula (7).

Of the compounds having the above-mentioned formula (1), a compound represented by the formula (9)

When the compound of the formula (1) of the present invention or the acid addition salt thereof is used as a therapeutic agent to treat patients with cardiac malfunctions such as arrhythmia and cardiac insufficiency, the

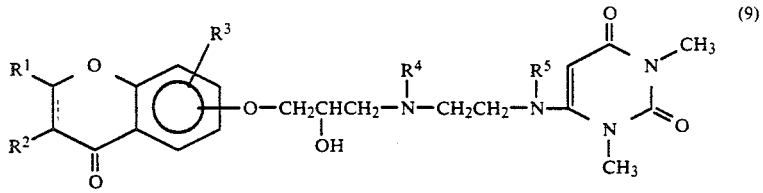

[wherein $R^1$, $R^2$, $R^3$, $R^4$, $R^5$ and $\doubleequals$ are defined as in the aforesaid formula (1)] can be prepared by a process containing the following step (f):

Step (f)

A compound of the formula (8)

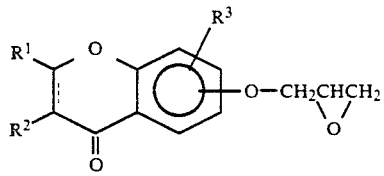

[wherein $R^1$, $R^2$, $R^3$ and $\doubleequals$ are defined as in the aforesaid formula (1)] is mixed with a compound of the formula (4) without using any solvent, or alternatively they are dissolved or suspended in a suitable solvent or dispersant, and reaction is then carried out, whereby the compound of the formula (9) can be obtained.

This reaction is effected at a temperature in the range of from room temperature to the reflux temperature of the reaction mixture, and for example, it can be selected from the range of from 20° to 150° C.

The suitable solvent or dispersant used in the reaction can be optionally selected, so long as it is inactive to the reaction solution. Examples of the solvent and dispersant include what are enumerated in the preceding paragraph regarding the step (a).

On the other hand, a pharmaceutically acceptable acid addition salt of the compound of the above-mentioned formula (1) can be produced by allowing the compound of the formula (1) to react with an inorganic or organic acid such as hydrochloric acid, hydrobromic acid, phosphoric acid, sulfuric acid, acetic acid, citric acid, maleic acid, fumaric acid, oxalic acid or methanesulfonic acid in water, an organic solvent or a mixture thereof.

dose and form of the agent depend on properties of the compound of the present invention which is used as an active ingredient and depend on symptoms of the patients to be treated. For example, the therapeutic agent can be orally administered in a dose of from 1 to 1,000 mg/day for an adult in the form of tablets, granules, powders, suspensions or capsules, or parenterally in the form of depositories, injections, fluids for infusion, inhalations or plasters.

General processes for producing pharmaceutical compositions of the present invention include a method in which the compound of the present invention is dissolved in an appropriate amount of an oil selected from the group consisting of cotton seed oil, corn oil, peanut oil, olive oil and the like so as to prepare non-aqueous injections each containing 1 to 500 mg of the compound of the present invention; a method in which the compound of the present invention is either suspended or emulsified in water in the presence of an appropriate surfactant so as to prepare aqueous injections each containing 1 to 500 mg of the compound of the present invention; or a method in which lactose, crystallized cellulose, corn starch or the like is added to the compound of the present invention and magnesium stearate is finally added thereto in order to prepare tablets each containing 1 to 1,000 mg of the compound of the present invention. However, the pharmaceutical preparations of the present invention can be obtained by any ordinary method in addition to the above-mentioned methods.

Now, the present invention will be described in more detail in reference to examples, but the scope of the present invention should not be limited to these examples.

EXAMPLE 1

Preparation of 1,3-dimethyl-6-(4-[3-(3-methyl-4-oxo-4H-1-benzopyran-5-yl)oxypropyl]piperazine-1-yl)-2,4(1H,3H)-pyrimidinedione hydrochloride (compound 4)

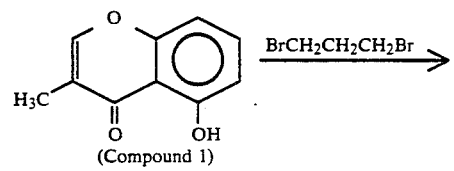
(Compound 1)

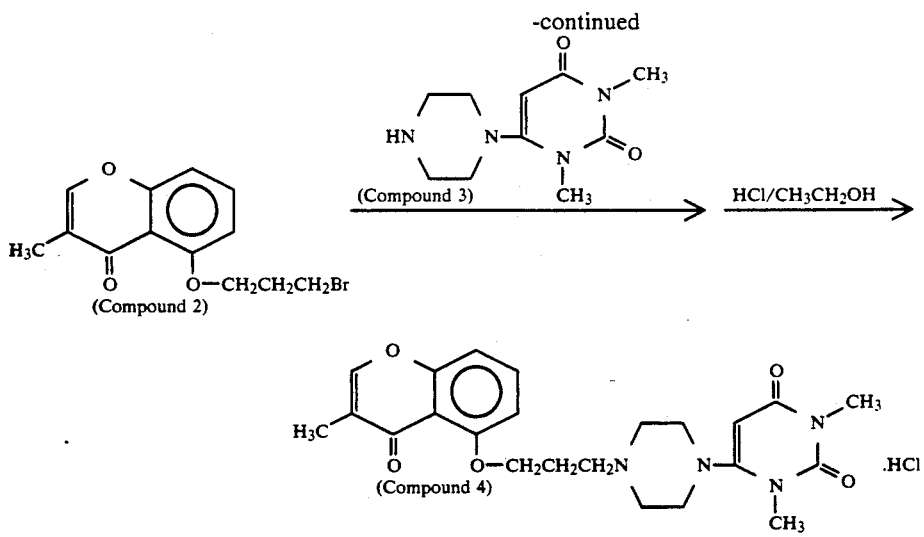

(1) Synthesis of 3-(3-methyl-4-oxo-4H-1-benzopyran-5-yl)oxypropyl bromide (Compound 2):

In 50 ml of dry N,N-dimethylformamide was dissolved 3.52 g of 3-methyl-5-hydroxy-4-oxo-4H-1-benzopyran (Compound 1), and after ice cooling, 0.88 g of 60% sodium hydride was added thereto, followed by stirring at room temperature for 15 minutes. To the mixture was added 8 ml of 1,3-dibromopropane, and reaction was then carried out at 60° C. for 1.5 hours. Afterward, 10 ml of water and then 3 ml of 1N hydrochloric acid were added to the reaction solution, and this solution was then concentrated under reduced pressure. The resulting residue was dissolved in chloroform, washed with water, dried over anhydrous sodium sulfate, and then concentrated under reduced pressure. The obtained residue was purified through a silica gel column chromatograph (chloroform:n-hexane=8:2 to 8:0 in volume ratio) to obtain an oily substance, and this substance was then treated with hexane, thereby obtaining 3.35 g (yield 56%) of 3-(3-methyl-4-oxo-4H-1-benzopyran-5-yl)oxypropyl bromide (Compound 2).

Analytical results of the obtained Compound 2:

Melting point: 102°–105° C. NMR (CDCl$_3$) δ ppm: 1.97 (3H, s), 2.47 (2H, m), 3.86 (2H, t), 4.21 (2H, t), 6.83 (1H, d), 7.01 (1H, d), 7.56 (1H, t), 7.71 (1H, s).

(2) Synthesis of 1,3-dimethyl-6-(4-[3-(3-methyl-4-oxo-4H-1-benzopyran-5-yl)oxypropyl]piperazine-1-yl)-2,4(1H,3H)-pyrimidinedione hydrochloride (Compound 4):

In 50 ml of dioxane, there were heated under reflux 1.78 g of the previously obtained, 3-(3-methyl-4-oxo-4H-1-benzopyran-5-yl)oxypropyl bromide (Compound 2), 1.34 g of 1,3-dimethyl-6-(piperazine-1-yl)-2,4(1H,3H)-pyrimidinedione (Compound 3) and 1.5 ml of triethylamine for 2 hours. After cooling and then filtration, the resultant filtrate was concentrated under reduced pressure, and the resultant residue was then dissolved in chloroform, washed with water, dried over anhydrous sodium sulfate, and then concentrated under reduced pressure. The thus obtained residue was purified through a silica gel column chromatograph (chloroform:methanol=100:2 to 100:10 in volume ratio) and then recrystallized from ethanol and ether in order to obtain 2.40 g (yield 91%) of 1,3-dimethyl-6-(4-[3-(3-methyl-4-oxo-4H-1-benzopyran-5-yl)oxypropyl]piperazine-1-yl)-2,4(1H,3H)-pyrimidinedione (the non-hydrochloride of Compound 4).

Analytical results of the obtained non-hydrochloride of Compound 4:

Melting point: 138°–139° C. NMR (CDCl$_3$) δ ppm: 2.00 (3H, s), 2.1–2.4 (2H, m), 2.6–3.1 (10H, m), 3.33 (3H, s), 3.40 (3H, s), 4.18 (2H, t), 5.31 (1H, s), 6.87 (1H, d), 7.04 (1H, d), 7.59 (1H, d), 7.76 (1H, d).

Values of elemental analysis (as C$_{23}$H$_{28}$N$_4$O$_5$): Calcd (%) C 62.71; H 6.41; N 12.72. Found (%): C 62.51; H 6.46; N 12.67.

Next, 2.3 g of this non-hydrochloride of Compound 4 was dissolved in 40 ml of ethanol, and a solution of 10% hydrogen chloride in ethanol was then added to the resultant solution so as to precipitate crystals. They were collected by filtration, thereby obtaining 2.24 g of 1,3-dimethyl-6-(4-[3-(3-methyl-4-oxo-4H-1-benzopyran-5-yl)oxypropyl]piperazine-1-yl)-2,4(1H,3H)-pyrimidinedionehydrochloride (Compound 4).

Analytical results of the obtained Compound 4:
Melting point: 250° C. or higher
Elemental analysis (as C$_{23}$H$_{28}$N$_4$O$_5$.HCl.¼H$_2$O):
Calcd. (%): C 57.38; H 6.18; N 11.64; Cl 7.36.
Found (%): C 57.50; H 6.18; N 11.55; Cl 7.60.
IR ν$_{max}^{KBr}$(cm$^{-1}$): 1640, 1195, 1160, 1070, 1005, 805, 760, 700.

EXAMPLE 2

Preparation of 1,3-dimethyl-6-(4-[3-(2,3-dimethyl-4-oxo-4H-1-benzopyran-5-yl)oxypropyl]piperazine-1-yl)-2,4(1H,3H)-pyrimidinedione oxalate (Compound 7)

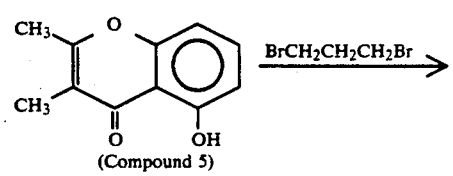

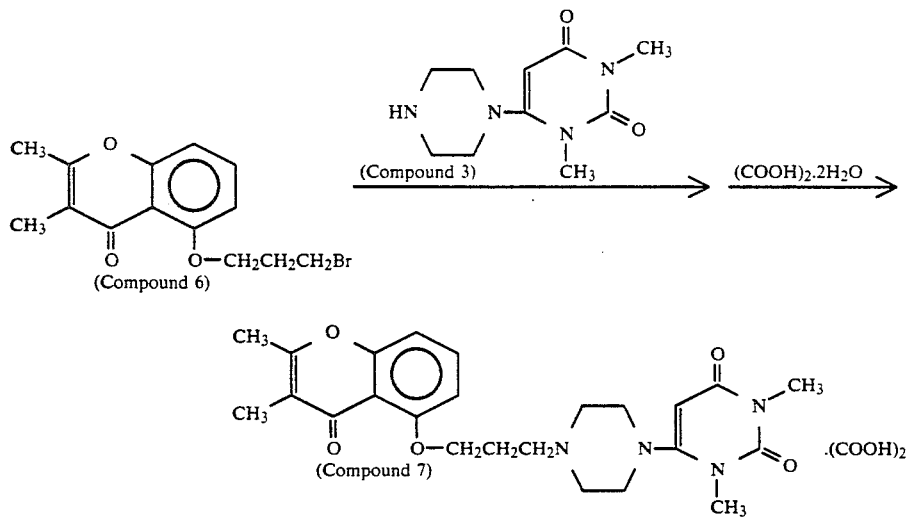

(1) Synthesis of 3-(2,3-dimethyl-4-oxo-4H-1-benzopyran-5-yl)oxypropyl bromide (Compound 6):

In 30 ml of dry tetrahydrofuran were dissolved 1.9 g of 2,3-dimethyl-5-hydroxy-4-oxo-4H-1-benzopyran (Compound 5), and 1.35 g of potassium t-butoxide were further added thereto. The mixture was stirred for 30 minutes, and the solvent was then distilled off under reduced pressure. To the resultant residue was added 30 ml of 1,3-dibromopropane, and reaction was then carried out at 100° C. for 3 hours. After cooling, 200 ml of chloroform was added thereto, followed by washing with water. The thus washed chloroform layer was dried over anhydrous sodium sulfate, and then concentrated under reduced pressure. The resultant residue was purified through a silica gel column chromatograph (hexane:chloroform:=7:3 to 10:0 in volume ratio) in order to obtain 0.94 g (yield 30%) of 3-(2,3-dimethyl-4-oxo-4H-1-benzopyran-5-yl)oxypropyl bromide (Compound 6).

Analytical results of the obtained Compound 6:

Melting point: 120° to 122° C.

Values of elemental analysis (as $C_{14}H_{15}BrO_3$) Calcd. (%): C 54.04; H 4.86; Br 25.68. Found (%): C 53.98; H 4.87; Br 24.90.

(2) Synthesis of 1,3-dimethyl-6-(4-[3-(2,3-dimethyl-4-oxo-4H-1-benzopyran-5-yl)oxypropyl]piperazine-1-yl)-2,4(1H,3H)-pyrimidinedione oxalate (Compound 7):

To 2 ml of N,N-dimethylformamide were added 0.78 g of the previously obtained 3-(2,3-dimethyl-4-oxo-4H-1-benzopyran-5-yl)oxypropyl bromide (Compound 6), 0.9 g of 1,3-dimethyl-6-(piperazine-1-yl)-2,4(1H,3H)-pyrimidinedione (Compound 3) and 3 ml of triethylamine, and the solution was then heated at 100° C. for 3 hours in order to carry out reaction. The resultant reaction solution was treated and then purified in the same manner as in Example 1-(2) to obtain 0.96 g (yield 84%) of 1,3-dimethyl-6-(4-[3-(2,3-dimethyl-4-oxo-4H-1-benzopyran-5-yl)oxypropyl]piperazine-1-yl)-2,4(1H,3H)-pyrimidinedione (the non-oxalate of Compound 7).

Analytical results of the obtained non-oxalate of Compound 7:

Melting point: 162 -163° C.

NMR ($CDCl_3$) δ ppm: 2.04 (3H, s), 2.14 (2H, m), 2.40 (3H, s), 2.5-3.1 (10H, m), 3.40 (3H, s), 3.44 (3H, s), 4.16 (2H, t), 5.28 (1H, s), 6.7-7.6 (3H, m).

Values of elemental analysis (as $C_{24}H_{30}N_4O_5$): Calcd. (%): C 63.42; H 6.65; N 12.33. Found (%): C 63.34; H 6.72; N 12.18.

Next, 0.9 g of this non-oxalate of Compound 7 was suspended in 30 ml of ethanol, and 0.5 g of oxalic acid dihydrate was added to the suspension, followed by stirring to form a uniform solution. This uniform solution was then concentrated under reduced pressure to about 5 ml, and 10 ml of ethyl ether was added thereto. The precipitated crystals were then collected by filtration, thereby obtaining 1.06 g of 1,3-dimethyl-6-(4-[3-(2,3-dimethyl-4-oxo-4H-1-benzopyran-5-yl)oxypropyl]-piperazine-1-yl)-2,4(1H,3H)-pyrimidinedione oxalate (Compound 7).

Analytical results of the obtained Compound 7:

Melting point: 148° C. (decomposed).

Elemental analysis (as $C_{24}H_{30}N_4O_5 \cdot (COOH)_2 \cdot H_2O$). Calcd. (%): C 55.51; H 6.09; N 9.96. Found (%): C 55.38; H 6.17; N 9.89.

IR $\nu_{max}^{KBr}$ (cm$^{-1}$): 3450, 3020, 1690, 1600, 1440, 1282, 1210, 1076, 980.

EXAMPLE 3

Preparation of 1,3-dimethyl-6-(4-[2-(2-phenyl-4-oxo-4H-1-benzopyran-7-yl)oxyethyl]piperazine-1-yl)-2,4-(1H,3H)-pyrimidinedione oxalate (Compound 10)

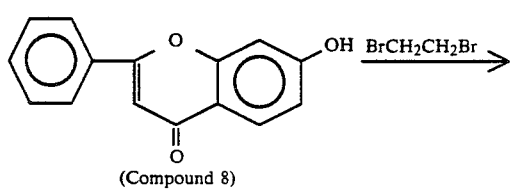

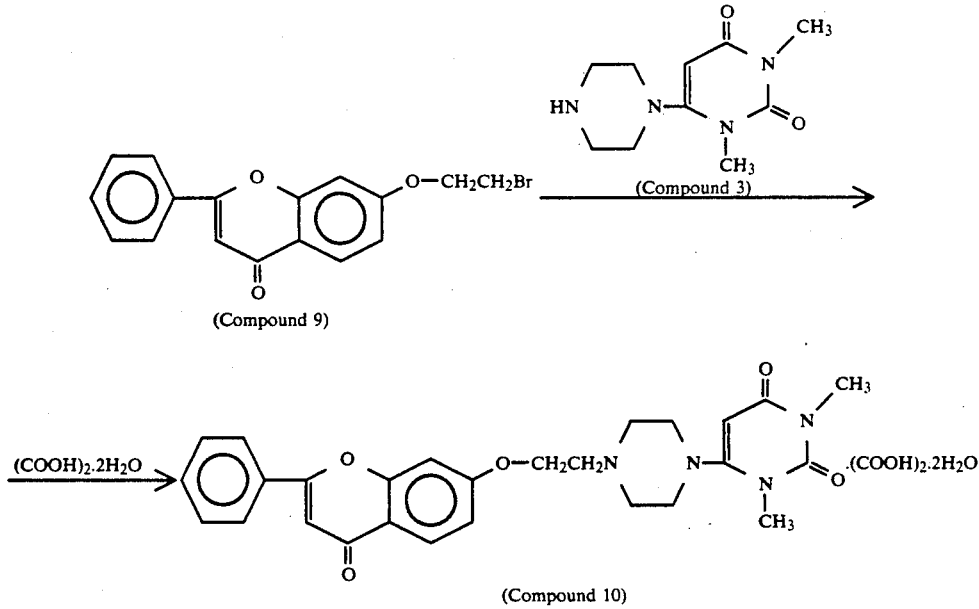

(1) Synthesis of 2-(2-phenyl-4-oxo-4H-1-benzopyran-7-yl)oxyethyl bromide (Compound 9):

In 3 ml of dry N,N-dimethylformamide was dissolved 0.5 g of 7-hydroxy-2-phenyl-4-oxo-4H-1-benzopyran (Compound 8), and 0.1 g of sodium hydride was then added to the solution, followed by stirring at room temperature for 30 minutes. Next, 1.03 ml of 1,2-dibromoethane was further added thereto, and reaction was carried out at 100° C. for 1 hour. The resultant reaction solution was poured into ice water and then extracted with ethyl acetate, and the resultant ethyl acetate layer was washed with water. The thus water-washed ethyl acetate layer was dried over anhydrous sodium sulfate, and then concentrated under reduced pressure. The obtained residue was purified through a silica gel column chromatograph (hexane:ethyl acetate=2:1 in volume ratio) and then crystallized from hexane in order to obtain 0.31 g (yield 43%) of 2-(2-phenyl-4-oxo-4H-1-benzopyran-7-yl)oxyethyl bromide (Compound 9).

Analytical results of the obtained Compound 9:

Melting point: 139°-141° C.

NMR (CDCl$_3$) δ ppm: 3.61 (2H, t), 4.32 (2H, t), 6.61 (1H, s), 6.84 (2H, m), 7.37 (3H, m), 7.6-8.2 (3H, m).

(2) Synthesis of 1,3-dimethyl-6-(4-[2-(2-phenyl-4-oxo-4H-1-benzopyran-7-yl)oxyethyl]piperazine-1-yl)-2,4(1H,3H)-pyrimidinedione oxalate (Compound 10):

In 1.5 ml of N,N-dimethylformamide, there were reacted 0.31 g of the previously obtained 2-(2-phenyl-4-oxo-4H-1-benzopyran-7-yl)oxyethyl bromide (Compound 9), 0.2 g of 1,3-dimethyl-6-(piperazine-1-yl)-2,4(1H,3H)-pyrimidinedione (Compound 3) and 0.4 ml of triethylamine at 100° C. for 1 hour. The resultant reaction solution was poured into ice water and then extracted with chloroform. The resultant chloroform layer was then washed with water, dried over anhydrous sodium sulfate, and then concentrated under reduced pressure. Afterward, the resultant residue was recrystallized from ethanol and hexane to obtain 0.30 g (yield 68%) of 1,3-dimethyl-6-(4-[2-(2-phenyl-4-oxo-4H-1-benzopyran-7-yl)oxyethyl]-piperazine-1-yl)-2,4(1H,3H)-pyrimidinedione (the nonoxalate of Compound 10).

Analytical results of the obtained non-oxalate of Compound 10:

Melting point: 187°-188° C.

NMR (CDCl$_3$) δ ppm: 2.6-3.1 (10H, m), 3.21 (3H, s), 3.33 (3H, s), 4.25 (2H, t), 5.18 (1H, s), 6.71 (1H, s), 7.04 (2H, m), 7.48 (3H, m), 8.00 (3H, m).

The non-oxalate of Compound 10 was converted into the oxalate in the same manner as in Example 2-(2).

Analytical results of the obtained oxalate of Compound 10:

Melting point: 203°-205° C. (decomposed).

Elemental analysis (as C$_{27}$H$_{28}$N$_4$O$_5$.(COOH)$_2$.2H$_2$O): Calcd (%) C: 56.67; H 5.58; N 9.12. Found (%): C 56.66; H 5.43; N 8.98.

IR $\nu_{max}^{KBr}$ (cm$^{-1}$): 3360, 2550, 1680, 1620, 1430, 1170, 820, 770, 720.

EXAMPLE 4

Preparation of 1,3-dimethyl-6-(2-[N-ethyl-N-[3-(3-methyl-4-oxo-4H-1-benzopyran-5-yl)oxypropyl]amino[ethylamino)-2,4(1H,3H)-pyrimidinedione oxalate (Compound 14)

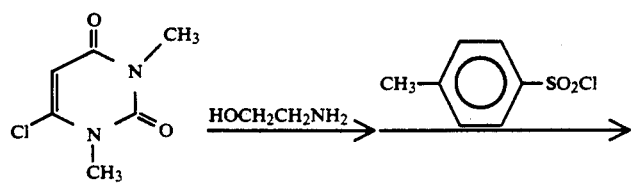

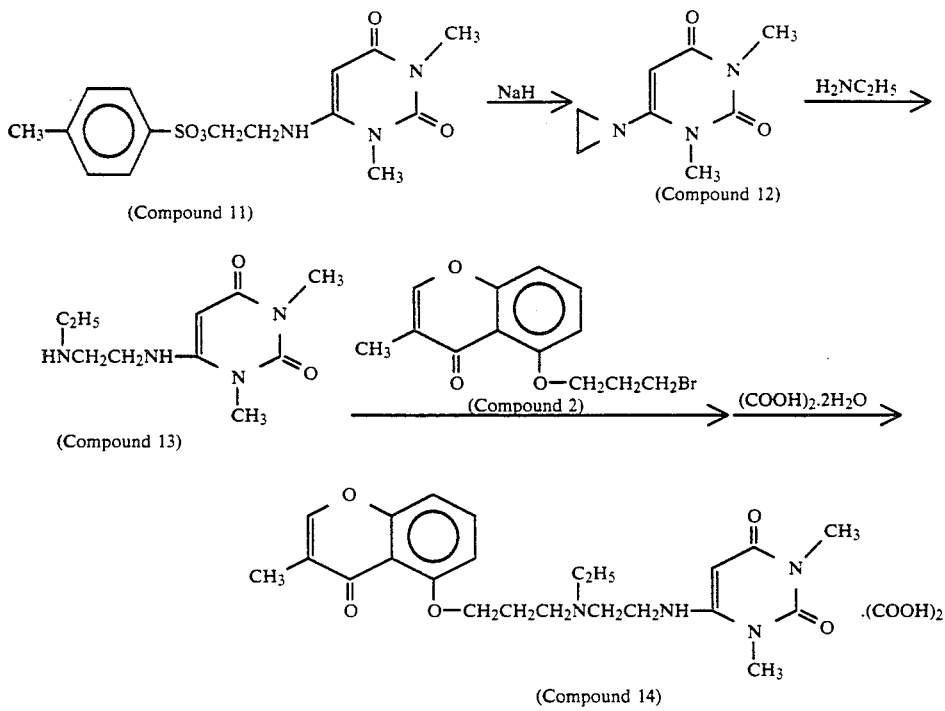

(1) Synthesis of 1,3-dimethyl-6-[2-(p-toluenesul-fonyloxy)ethylamino]-2,4(1H,3H)-pyrimidinedione (Compound 11):

On an oil bath, 35.0 g of 2-aminoethanol was heated up to 90° C., and it was removed from the oil bath, and 50.5 g of 6-chloro-1,3-dimethyl-2,4-dioxopyrimidine was added thereto in order to carry out reaction. This addition was effected at such a rate as to maintain a reaction temperature in the range of 90° to 110° C. After completion of the addition, the reaction mixture was stirred for 10 minutes, and 300 ml of dioxane/methanol (10/1 in volume ratio) was then added thereto. The mixture was allowed to stand overnight, and the resultant crystals were washed with a small, amount of dioxane and then dried, thereby obtaining 49.0 g of 1,3-dimethyl-6-(2-hydroxyethylamino)-2,4(1H,3H)-pyrimidinedione in the state of white crystals.

Next, the suspension prepared by suspending 49.0 g of the white crystals in 200 ml of pyridine was cooled to $-5°$ C., and 40.0 g of p-toluenesulfonyl chloride was added thereto at such a rate that a reaction temperature did not rise in excess of 5° C. In order to completely extinguish the turbidity of the reaction solution, 51.0 g of p-toluenesulfonyl chloride were additionally used.

Furthermore, the resultant reaction mixture was poured into 1.5 liters of ice water containing 70 g of $K_2CO_3$, and it was then allowed to stand overnight. The resultant crystals were collected by filtration, washed with water, and then dried under reduced pressure, thereby obtaining 50.5 g of 1,3-dimethyl-6-[2-(p-toluenesulfonyloxy)ethylamino]-2,4(1H,3H)-pyrimidinedione (Compound 11) in the state of light yellow crystals.

Analytical results of the obtained Compound 11:
Melting point: 146.0°–149.0° C.
IR $\nu_{max}^{KBr}$ (cm$^{-1}$): 3270, 1682, 1615, 1550, 1480, 1435, 1360, 1190, 1178, 1010, 903, 780.

(2) Synthesis of 6-(1-aziridinyl)-1,3-dimethyl-2,4(1H,3H)-pyrimidinedione (Compound 12):

To 150 ml of anhydrous dimethyl sulfoxide containing 47.2 g of the previously obtained Compound 11 were slowly added 6.24 g of 60% oily sodium hydride at room temperature, and the resulting mixture was then stirred vigorously at room temperature for 5 hours. After cooling, a small amount of water was added thereto so as to bring the reaction to an end. The reaction mixture was poured into 1 liter of water containing 70 g of potassium carbonate, and then extracted with 200 ml of chloroform three times. Afterward, a joined organic layer was dried over anhydrous sodium sulfate and then concentrated, and 300 ml of ether were added to the resultant concentrate. The mixture was then allowed to stand overnight.

Light yellow crystals which were precipitated by the overnight standing were collected by filtration, washed with ether, and then dried under reduced pressure in order to obtain 15.2 g of 6-(1-aziridinyl)-1,3-dimethyl-2,4(1H,3H)-pyrimidinedione (Compound 12).

- Analytical results of the obtained Compound 12:
Melting point: 126.0°–126.5° C.
IR $\nu_{max}^{KBr}$ (cm$^{-1}$): 1750, 1650, 1612, 1470, 1440, 1305, 1160, 783, 490.
$^1$H-NMR (CDCl$_3$) δ ppm: 2.34 (s, 4H), 3.35 (s, 3H), 3.56 (s, 3H), 5.25 (s, 1H).

(3) Synthesis of N-(1,3-dimethyl-2,4-dioxopyrimidine-6-yl)-N'-ethylethylenediamine (Compound 13):

To 7.6 g of a 70% aqueous ethylamine solution was added 0.91 g of the previously obtained Compound 12, followed by stirring at room temperature for 3 hours. After completion of the stirring treatment, the reaction solution was concentrated under reduced pressure, and 80 ml of ethanol were added to the resultant residue. Then, the ethanol solution was further concentrated under reduced pressure. Ether was added to the resultant residue, and crystallization was then effected. Afterward, a mixed solution of ether and hexane in a ratio of 1:1 (volume ratio) was added thereto. The crystals were then collected by filtration to obtain 1.07 g of N-(1,3-dimethyl-2,4-dioxopyrimidine-6-yl)-N'-ethylethylene-diamine (Compound 13).

Analytical results of the obtained Compound 13:
Melting point 110°–113° C.

NMR (CDCl$_3$) δ ppm: 1.12 (3H, s), 1.27 (1H, s), 2.65 (2H, q), 2.95 (2H, m), 3.06 (2H, m), 3.31 (3H, s), 3.40 (3H, s), 4.80 (1H, s), 5.55 (1H, s).

(4) Synthesis of 1,3-dimethyl-6-(2-[N-ethyl-N-[3-(3-methyl-4-oxo-4H-1-benzopyran-5-yl)oxypropyl]amino]-ethylamino)-2,4(1H,3H)-pyrimidinedione oxalate (Compound 14):

To 5 ml of dimethyl sulfoxide were added 0.52 g of the previously obtained N-[1,3-dimethyl-2,4-dioxopyrimidine-6-yl]-N'-ethylethylenediamine (Compound 13), 0.7 g of 3-(3-methyl-4-oxo-4H-1-benzopyran-5-yl)oxypropyl bromide (Compound 2) and 0.5 ml of propyl]amino]ethylamino)-2,4(1H,3H)-pyrimidinedione oxalate (Compound 14).

Analytical results of the obtained Compound 14:
Melting point: 193.5°–195.2° C. (decomposed).
Elemental analysis (as $C_{23}H_{30}N_4O_5 \cdot (COOH)_2$).
Calcd. (%): C 56.38; H 6.06; N 27.04. Found (%): C 56.71; H6.51; N 17.18.

IR $\nu_{max}^{KBr}$ (cm$^{-1}$): 3430, 1755, 1688, 1640, 1607, 1482, 1383, 1262, 1165, 1055, 775.

EXAMPLE 5

Preparation of 1,3-dimethyl-6-(2-[N-hydroxyethyl-N-[3-(2-phenyl-3-methyl-4oxo-4H-1-benzopyran-5yl)oxypropyl]amino]ethylamino)-2,4(1H,3H)-pyrimidinedione oxalate (Compound 17)

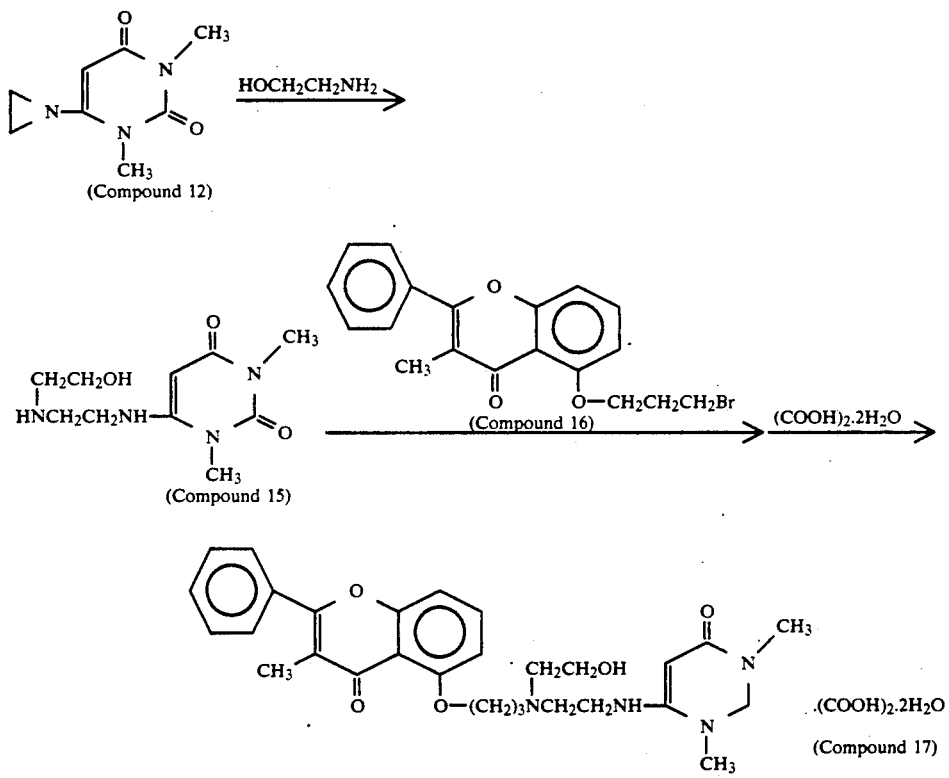

triethylamine, and reaction was carried out at 100° C. for 6 hours. The resultant reaction solution was cooled, and the formed white crystals were collected by filtration, washed with water, and then dried, thereby obtaining 0.56 g of 1,3-dimethyl-6-(2-[N-ethyl-N-[3-(3-methyl-4-oxo-4H-1-benzopyran-5-yl)oxypropyl]amino]ethylamino)-2,4(1H,3H)-pyrimidinedione (the non-oxalate of Compound 14).

Analytical results of the obtained non-oxalate of Compound 14:

NMR (CDCl$_3$) δ ppm: 1.11 (3H, t), 1.99 (3H, s), 1.95–2.30 (2H, m), 2.40–2.90 (4H, m), 2.93 (3H, s), 2.91–3.20 (4H, m), 3.24 (3H, s), 4.11 (2H, t), 4.45 (1H, s), 5.12 (1H, brs), 6.76 (1H, d), 6.95 (1H, d), 7.52 (1H, t), 7.69 (1H, s).

Next, this non-oxalate of Compound 14 was treated with oxalic acid dihydrate in the same manner as in Example 2-(2) to obtain 0.5 g of 1,3-dimethyl-6-(2-[N-ethyl-N-[3-(3-methyl-4-oxo-4H-1-benzopyran-5-yl)oxy- (1) Synthesis of 1,3-dimethyl-6-[2-(2-hydroxyethylamino)ethylamino]-2,4(1H,3H)-pyrimidinedione (Compound 15):

To 45 ml of acetonitrile were added 0.81 g of 6-(1-aziridinyl)-1,3-dimethyl-2,4(1H,3H)-pyrimidinedione (Compound 12), 1 ml of aminoethanol and 5 mg of p-toluenesulfonic acid so as to form a uniform solution, and this solution was then concentrated under reduced pressure. The resultant residue was then heated at 70° C. for 3 hours. After cooling, ether was added thereto, followed by stirring, and the precipit,ated crystals thus obtained were collected by filtration and then recrystallized from ethanol and ether, thereby obtaining 1.02 g (yield 94%) of 1,3-dimethyl-6-[2-(2-hydroxyethylamino)-ethylamino]-2,4(1H,3H)-pyrimidinedione (Compound 15).

Melting point of the obtained Compound 15: 146°–148° C.

(2) Synthesis of 1,3-dimethyl-6-(2-[N-hydroxyethyl-N-[3-(2-phenyl-3-methyl-4-oxo-4H-1-benzopyran-5- yl)oxypropyl]amino]ethylamino)-2,4(1H,3H)-pyrimidinedione oxalate (Compound 17):

In 5 ml of N,N-dimethylformamide, reaction was carried out at 90° C. for 1 hour among 0.68 g of 1,3-dimethyl-6-[2-(2-hydroxyethylamino)ethylamino]-2,4-(1H,3H)-pyrimidinedione (Compound 15), 0.96 g of 3-(2-phenyl-3-methyl-4-oxo-4H-1-benzopyran-5-yl)oxypropyl bromide (Compound 16) and 1 ml of triethylamine. The resultant reaction solution was concentrated under reduced pressure, and the residue was dissolved in chloroform and then washed with water. The thus water-washed chloroform layer was dried over anhydrous sodium sulfate, and then purified through a silica gel column chromatograph (chloroform:methanol=98:2 to 96:4 in volume ratio) in odrer to obtain 0.75 g (yield 55%) of 1,3-dimethyl-6-(2-[N-hydroxyethyl-N-[3-(2-phenyl-3-methyl-4-oxo-4H-1-benzopyran-5-yl)oxypropyl]amino]ethyl-amino)-2,4(1H,3H)-pyrimidinedione (the non-oxalate of Compound 17).

Analytical results of the obtained non-oxalate of the Compound 17:

Melting point: 158°–159° C.

NMR (CDCl₃) δ ppm: 2.09 (3H, s), 2.67–3.22 (10H, m), 3.10 (3H, s), 3.19 (3H, s), 3.71 (2H, m), 3.16 (2H, m), 4.62 (1H, s), 5.78 (1H, b-s), 6.70–7.72 (8H, m).

The thus obtained non-oxalate of Compound 17 was treated with oxalic acid dihydrate in the same manner as in Example 2-(2) to obtain 1,3-dimethyl-6-(2-[N-hydroxyethyl-N-[3-(2-phenyl-3-methyl-4-oxo-4H-1-benzopyran-5-yl)oxypropyl]amino]ethylamino)-2,4(1H,3H)-pyrimidinedione oxalate (Compound 17).

Analytical results of the obtained Compound 17:

Melting point: 176.5° C. (decomposed).

Elemental analysis (as C₂₉H₃₄N₄O₆·(COOH)₂·2H₂O).
Calcd. (%): C 56.36; H 6.10; N 8.48. Found (%): C 56.54; H 5.97; N 8.23.

IR $\nu_{max}^{KBr}$ (cm⁻¹): 3380, 3230, 2980, 1680, 1630, 1615, 1602, 1533, 1456, 1392, 1090.

EXAMPLE 6

Preparation of 1,3-dimethyl-6-(4-[3-(2-phenyl-4-oxo-2,3-dihydro-4H-1-benzopyran-5-yl)oxypropyl]piperazine-1-yl)-2,4(1H,3H)-pyrimidinedione oxalate

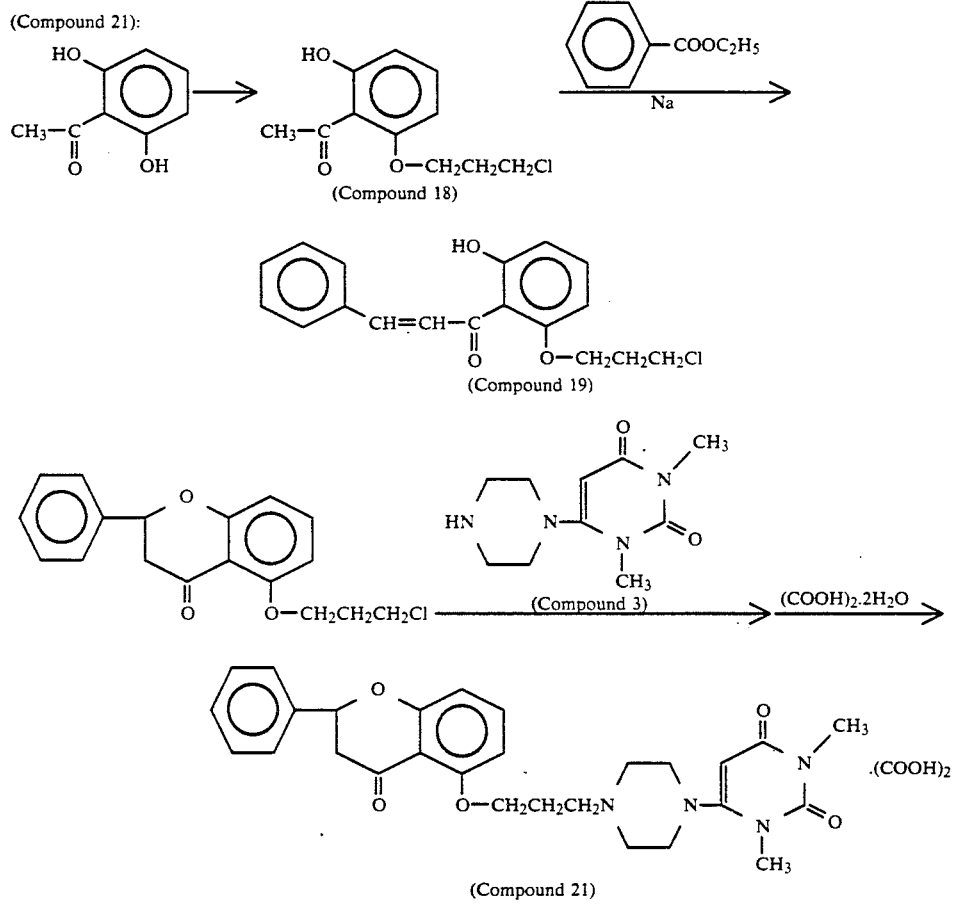

(Compound 21)

(1) Synthesis of 2-(3-chloropropoxy)-6-hydroxyacetophenone (Compound 18):

In 250 ml of methyl ethyl ketone were dissolved 10 g of 2,6-dihydroxyacetophenone and 16 g of 1-bromo-3-chloropropane, and 7.4 g of anhydrous potassium carbonate was further added thereto Then, the solution was heated under reflux for 30 hours. After cooling, insolubles were removed therefrom by filtration, and the filtrate was then concentrated to dryness. The resultant residue was washed with a mixed solution of ethyl ether and ethanol in a ratio of about 10:1 (volume ratio) in order to obtain crude 2-(3-chloropropoxy)-6-hydroxyacetophenone (Compound 18). This Compound 18 was used for the reaction in the following paragraph (2) without purifying.

(2) Synthesis of 2'-(3-chloropropoxy)-6'-hydroxychalcone (Compound 19):

In 50 ml of ethyl benzoate was dissolved the total amount of the previously obtained crude 2-(3-chloropropoxy)-6hydroxyacetophenone (Compound 18), and fine grains of metallic sodium were added thereto little by little. After exothermic phenomenon was not observed any more, reaction was carried out at 120° C. for 1 hour. The resulting reaction solution was then allowed to stand to cool it, and 50 ml of methanol was added thereto. Afterward, the solution was poured into ice water, and the resultant precipitate was collected by filtration, and then washed with water to obtain crude 2'-(3-chloropropoxy)-6'-hydroxychalcone (Compound 19). This Compound 19 was used for the reaction described in the following paragraph (3) without purifying.

(3) Synthesis of 2-phenyl-5-(3-chloropropoxy)-4-oxo-2,3-dihydro-4H-1-benzopyran (Compound 20):

The total amount of the previously obtained crude 2'-(3-chloropropoxy)-6'-hydroxychalcone (Compound 19) was dissolved in 100 ml of ethanol, and 2 ml of concentrated sulfuric acid was added thereto and reaction was then carried out at 80° C. for 3 hours. The resultant reaction solution was poured into 800 ml of water, and a supernatant was then removed therefrom. The left oily residue was dissolved in ethyl acetate, and then washed with water. The thus water-washed ethyl acetate layer was dried over anhydrous sodium sulfate, and then purified through a silica gel column chromatograph (hexane:ethyl acetate=4:1 in volume ratio) in order to obtain 2.7 g of 2-phenyl-5-(3-chloropropoxy)-4-oxo-2,3-dihydro-4H-1-benzopyran (Compound 20).

(4) Synthesis of 1,3-dimethyl-6-(4-[3-(2-phenyl-4-oxo-2,3-dihydro-4H-1-benzopyran-5-yl)oxypropyl]piperazine-1-yl)-2,4(1H,3H)-pyrimidinedione oxalate (Compound 21):

In 10 ml of N,N-dimethylformamide, reaction was carried out at 100° C. for 8 hours among 2.5 g of the previously obtained 2-phenyl-5-(3-chloropropoxy)-4-oxo-2,3-dihydro-4H-1-benzopyran (Compound 20), 1.2 g of 1,3-dimethyl-6-(piperazine-1-yl)-2,4(1H,3H)-pyrimidinedione (Compound 3), 1.0 g of tetraethylammonium bromide and 2.0 ml of triethylamine. The resultant reaction solution was concentrated under reduced pressure, and the residue was then dissolved in chloroform, washed with water, dried over anhydrous sodium sulfate, and then purified through a silica gel column chromatograph (chloroform:methanol=40:1 in volume ratio), thereby obtaining 0.80 g of 1,3-dimethyl-6-(4-[3-(2-phenyl-4-oxo-2,3-dihydro-4H-1-benzopyran-5-yl)oxypropyl]piperazine-1-yl)-2,4(1H,3H)-pyrimidinedione (the non-oxalate of Compound 21).

Analytical results of the obtained non-oxalate of the Compound 21:

NMR (CDCl$_3$) $\delta$ ppm: 2.1 (4H, m), 2.5-3.1 (10H, m), 3.29 (3H, s), 3.39 (3H, s), 4.41 (2H, t), 5.36 (1H, s), 7.0-7.9 (8H, m).

The non-oxalate of Compound 21 was treated with oxalic acid dihydrate in the same manner as in Example 2-(2) to obtain 0.79 g of 1,3-dimethyl-6-(4-[3-(2-phenyl-4-oxo-2,3-dihydro-4H-1-benzopyran-5-yl)oxypropyl]piperazine-1-yl)-2,4(1H,3H)-pyrimidinedione oxalate (Compound 21).

Analytical results of the obtained Compound 21:
Melting point: 168°-170° C.
Elemental analysis (as $C_{28}H_{32}N_4O_5$ (COOH)$_2$.3H$_2$O). Calcd. (%): C 55.55; H 6.22; N 8.64. Found (%) C 55.54; H 6.19; N 8.60.

IR $\nu_{max}^{KBr}$ (cm$^{-1}$): 3400, 3000, 1740, 1690, 1640, 1480, 1280, 1100, 860, 800, 760.

EXAMPLE 7

Preparation of 1,3-dimethyl-6-(4-[3-[2-(pyridine-4-yl)-4-oxo-4H-1-benzopyran-5-yl]oxypropyl]piperazine-1-yl)-2,4(1H,3H)-pyrimidinedione dihydrochloride (Compound 25): (Compound 25):

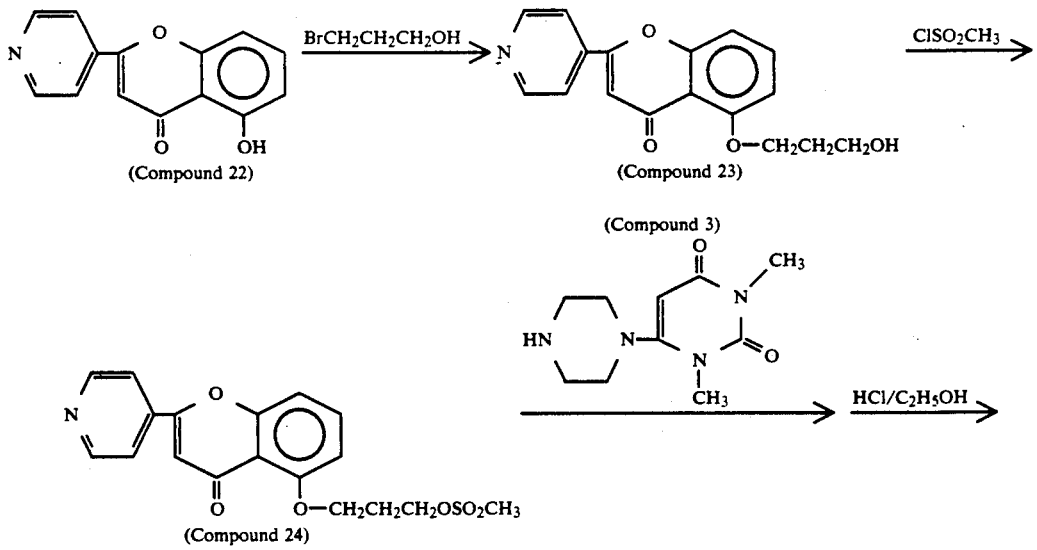

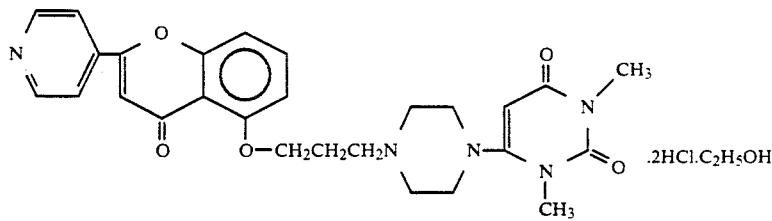

(Compound 25)

(1) Synthesis of 3-[2-(pyridine-4-yl)-4-oxo-4H-1-benzopyran-5-yl]oxypropanol (Compound 23):

In 100 ml of dry tetrahydrofuran were dissolved 3.59 g of 5-hydroxy-2-(pyridine-4-yl)-4-oxo-4H-1-benzopyran (Compound 22), and 1.68 g of potassium t-butoxide was further added thereto. After stirring for 15 minutes, the solvent was distilled off under reduced pressure. Next, 90 ml of N,N-dimethylformamide and 2.29 g of 3-bromopropanol were added to the resultant residue, and reaction was then carried out at 60° C. for 3.5 hours. The resultant reaction solution was concentrated under reduced pressure, and the residue was dissolved in chloroform and then washed with water. The thus water-washed chloroform layer was concentrated under reduced pressure, and the resultant residue was purified through a silica gel column chromatograph (chloroform:methanol=100:1 to 100:7 in volume ratio) and then crystallized from ethanol, thereby obtaining 3.56 g (yield 80%) of 3-[2-(pyridine-4-yl)-4-oxo-4H-1-benzopyran-5-yl]oxy-propanol (Compound 23).

Melting point of the obtained Compound 23: 197°-200° C.

(2) Synthesis of 3-[2-(pyridine-4-yl)-4-oxo-4H-1-benzopyran-5-yl]oxy-1-methanesulfonyloxypropane (Compound 24):

In 60 ml of chloroform were dissolved 2.08 g of 3-[2-(pyridine-4-yl)-4-oxo-4H-1-benzopyran-5-yl]oxypropanol (Compound 23), and 3.23 g of methanesulfonyl chloride and 2.5 ml of triethylamine were further added thereto and reaction was then carried out at 40° to 50° C. for 4 hours. After cooling, the reaction solution was washed with water, and the resultant chloroform layer was dried over anhydrous sodium sulfate. Afterward, most of chloroform was distilled off under reduced pressure, and ethanol was added to the remaining solution. The deposited crystals were collected by filtration to obtain 2.17 g (yield 83%) of 3-[2-(pyridine-4-yl)-4-oxo-4H-1-benzopyran-5-yl]oxy-1-methanesulfonyloxypropane (Compound 24).

Melting point of the obtained Compound 24: 171°-172° C.

(3) Synthesis of 1,3-dimethyl-6-(4-[3-[2-(pyridine-4-yl)-4-oxo-4H-1-benzopyran-5-yl]oxypropyl]pyperazine-1-yl)-2,4(1H,3H)-pyrimidinedione dihydrochloride (Compound 25):

In 50 ml of dioxane, there were heated under reflux for 4 hours 2.12 g of 3-[2-(pyridine-4-yl)-4-oxo-4H-1-benzopyran-5-yl]oxy-1-methanesulfonyloxypropane (Compound 24), 1 ml of triethlamine and 1.95 g of 1,3-dimethyl-6-(piperazine-1-yl)-2,4(1H,3H)-pyrimidinedione (Compound 3). The resultant reaction solution was then concentrated, and the resultant residue was dissolved in chloroform and then washed with water. Afterward, the water-washed chloroform layer was dried over anhydrous sodium sulfate and then purified through a silica gel column chromatograph (chloroform:methanol=100:1 to 100:15 in volume ratio) and then recrystallized from ethanol, thereby obtaining 2.36 g (yield 83%) of 1,3-dimethyl-6-(4-[3-[2-(pyridine-4-yl)-4-oxo-4H-1-benzopyran-5-yl]oxypropyl]pyperazine-1-yl)-2,4(1H,3H)-pyrimidinedione (the non-hydrochloride of Compound 25).

Analytical results of the obtained non-hydrochloride of Compound 25:

Melting point: 193°-194° C. Values of elemental analysis (as $C_{27}H_{29}N_5O_5$) Calcd. (%): C 64.40; H 5.81; N 13.91. Found (%): C 64.37; H 6.00; N 13.54.

NMR (CDCl$_3$) δ ppm: 2.0-2.3 (2H, m), 2.5-3.9 (10H, m), 3.30 (3H, s), 3.37 (3H, s), 4.70 (2H, t), 5.20 (1H, s), 6.8-7.9 (6H, m), 8.78 (1H, d), 8.82 (1H, d).

The non-hydrochloride of Compound 25 was dissolved in ethanol, and a solution of 10% hydrogen chloride in ethanol was then added thereto, thereby obtaining 2.71 g of 1,3-dimethyl-6-(4-[3-[2-(pyridine-4-yl)-4-oxo-4H-1-benzopyran-5-yl]oxypropyl]pyperazine-1-yl)-2,4(1H,3H)-pyrimidinedione dihydrochloride.C$_2$H$_5$OH (Compound 25).

Analytical results of the obtained Compound 25:
Melting point: 245°-255° C.

Elemental analysis (as $C_{27}H_{29}N_5O_5.2HCl.C_2H_5OH$): Calcd. (%): C 55.95; H 5.99; N 11.25, Cl 11.39. Found (%): C 55.76; H 6.15; N 11.36, Cl 11.49.

IR $\nu_{max}^{KBr}$ (cm$^{-1}$): 3400, 1640, 1460, 1270, 1200, 1090, 830, 760.

EXAMPLE 8

Preparation of 1,3-dimethyl-6-(4-[3-(2-phenyl-4-oxo-4H-1-benzopyran-6-yl)oxypropyl]piperazine-1-yl)-2,4(1H,3H)-pyrimidinedione oxalate (Compound 28):

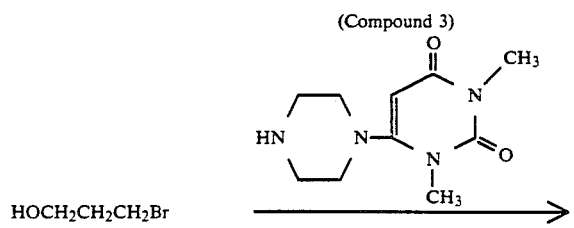

(Compound 3)

HOCH$_2$CH$_2$CH$_2$Br ⟶

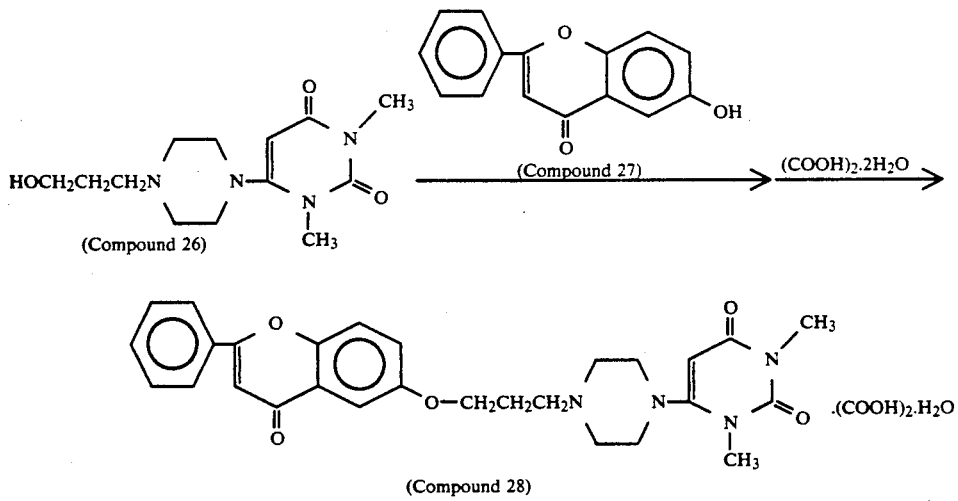

(1) Synthesis of 1,3-dimethyl-6-[4-(3-hydroxypropyl)-piperazine-1-yl]-2,4(1H,3H)-pyrimidinedione (Compound 26):

In 250 ml of ethanol, reaction was carried out for 20 hours between 14.1 g of 1,3-dimethyl-6-(piperazine-1-yl)-2,4(1H,3H)-pyrimidinedione (Compound 3) and 11.7 g of 3-bromo-1-propanol and 13 g of triethylamine by heating them under reflux. After completion of the reaction, the reaction mixture was concentrated to dryness, and the resultant residue was dissolved in 300 ml of chloroform and then washed with 100 ml of water twice. Afterward, the washed organic layer was dried over anhydrous magnesium sulfate and then treated with under reduced pressure, and the solvent was distilled off, thereby obtaining 20.5 g of a crude product. Next, ether was added to this crude product so as to achieve crystallization. The resultant crystals were recovered, washed and then dried to obtain 12.4 g (yield 69.8%) of 1,3-dimethyl-6-[4-(3-hydroxypropyl)piperazine-1-yl]-2,4(1H,3H)-pyrimidinedione (Compound 26).

Analytical results of the obtained Compound 26:
Melting point: 119°–121° C.
NMR (CDl$_3$) δ ppm: 1.8 (dt, 2H), 2.7 (m, 6H), 3.02 (m, 4H), 3.36 (s, 3H), 3.43 (s, 3H), 3.82 (t, 2H), 4.34 (br, 1H), 5.26 (s, 1H).
IR νhd max$^{KBr}$ (cm$^{-1}$): 3380, 3180, 2830, 1695, 1650, 1605, 1440, 1213, 1068, 1000, 921, 760.

(2) Synthesis of 1,3-dimethyl-6-(4-[3-(2-phenyl-4-oxo-4H-1-benzopyran-6-yl)oxypropyl]piperazine-1-yl)-2,4(1H,3H)-pyrimidinedione oxalate (Compound 28):

In 40 ml of tetrahydrofuran were dissolved 0.84 g of 6-hydroxy-2-phenyl-4-oxo-4H-1-benzopyran (Compound 27), 0.5 g of the previously obtained 1,3-dimethyl-6-[4-(3-hydroxypropyl)piperazine-1-yl]-2,4(1H,3H)-pyrimidinedione (Compound 26) and 0.66 g of triphenylphosphine. Then, 0.4 ml of diethyl azodicarboxylate was added to the solution, followed by stirring for 1 hour. The resultant reaction solution was concentrated under reduced pressure, and the resultant residue was purified through a silica gel column chromatograph (chloroform:methanol=40:1 in volume ratio) to obtain 0.41 g (yield 43%) of 1,3-dimethyl-6-(4-[3-(2-phenyl-4-oxo-4H-1-benzopyran-6-yl)oxypropyl]piperazine-1-yl)-2,4(1H,3H)-pyrimidinedione (the non-oxalate of Compound 28).

Analytical results of the obtained non-oxalate of the Compound 28:
NMR (CDCl$_3$) δ ppm: 2.13 (2H, m), 2.69–3.05 (10H, m), 3.30 (3 H, s), 3.35 (3H, s), 4.29 (2H, m), 5.30 (1H, s), 7.33–8.19 (9H, m).

The non-oxalate of Compound 28 was treated with oxalic acid dihydrate in the same manner as in Example 2-(2) to obtain 0.20 g of 1,3-dimethyl-6-(4-[3-(2-phenyl-4-oxo-4H-1-benzopyran-6-yl)oxypropyl]piperazine-1-yl)-2,4(1H,3H)-pyrimidinedione oxalate, (Compound 28).

Analytical results of the obtained Compound 28:
Melting point: 220°–222° C. (decomposed).
Elemental analysis (as $C_{28}H_{30}N_4O_5 \cdot (COOH)_2H_2O$).
Calcd. (%): C 59.01; H 5.61; N 9.18. Found (%): C 58.71; H 5.43; N 9.47.
IR ν$_{max}$$^{KBr}$ (cm$^{-1}$): 3400, 1700, 1630, 1600, 1430, 1250, 1130, 780, 760, 700.

EXAMPLE 9

Preparation of 1,3-dimethyl-6-(4-[2-(2-phenyl-4-oxo-4H-1-benzopyran-6yl)oxyethyl]piperazone-1-yl)-2,4(1H,3H)-pyrimidinedione oxalate (Compound 31):

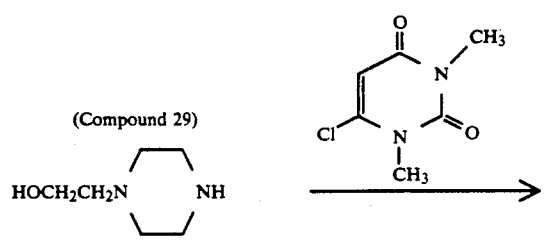

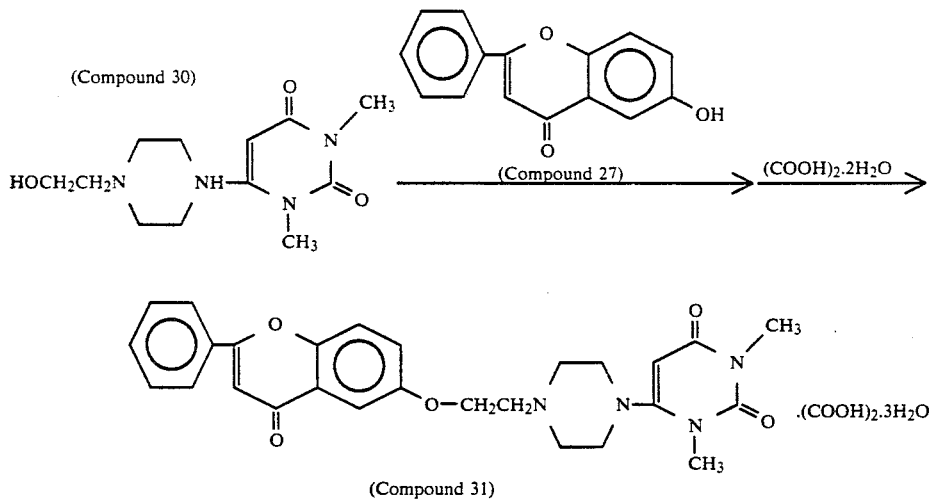

(1) Synthesis of 1,3-dimethyl-6-[4-(2-hydroxyethyl)-piperazine-1-yl]-2,4(1H,3H)-pyrimidinedione (Compound 30):

In 70 ml of isopropyl alcohol, there were heated under reflux for 3 hours 4 ml of 1-(2-hydroxyethyl)piperazine (Compound 29), 2.7 g of 6-chloro-1,3-dimethyl-2,4-dioxopyrimidine and 12 ml of triethylamine. The resultant reaction solution was concentrated under reduced pressure, and the resultant residue was dissolved in 60 ml of chloroform and then washed with 20 ml of water. After the water washing, the resultant chloroform layer was dried over anhydrous sodium sulfate and then concentrated under reduced pressure. A small amount of methanol and 50 ml of ether were added to the resultant light yellow oily residue, and the solution was stirred to form crystals. The thus formed crystals were then collected by filtration, thereby obtaining 3.72 g (yield 90%) of 1,3-dimethyl-6-[4-(2-hydroxyethyl)piperazine-1-yl]-2,4(1H,3H)-pyrimidinedione (Compound 30).

Analytical results of the obtained Compound 30:

Values of elemental analysis (as $C_{12}H_{20}N_4O_3$). Calcd. (%): C 53.70; H 7.51; N 20.91. Found (%): C 53.47; H 7.83; N 20.96.

(2) Synthesis of 1,3-dimethyl-6-(4-[2-(2-phenyl-4-oxo-4H-1-benzopyran-6-yl)oxyethyl]piperazine-1-yl)-2,4(1H,3H)-pyrimidinedione oxalate (Compound 31):

The same procedure as in Example 8-(2) was effected so as to react and treat 0.8 g of 1,3-dimethyl-6-[4-(2-hydroxyethyl)piperazine-1-yl]-2,4(1H,3H)-pyrimidinedione (Compound 30), 1.19 g of 6-hydroxy-2-phenyl-4-oxo-4H-1-benzopyran (Compound 27), 40 ml of tetrahydrofuran containing 1.05 g of triphenylphosphine and 0.63 ml of diethyl azodicarboxylate, in order to obtain 0.89 g (yield 58%) of 1,3-dimethyl-6-(4-[2-(2-phenyl-4-oxo-4H-1-benzopyran-6-yl)oxyethyl]piperazine-1-yl)-2,4(1H,3H)-pyrimidinedione (the non-oxalate, of Compound 31).

Analytical results of the obtained non-oxalate of the Compound 30:

Melting point: 133°–134° C.

NMR (CDCl$_3$) δ ppm: 2.5–3.1 (10H, m), 3.30 (3H, s), 3.36 (3H, s), 4.22 (2H, t), 5.14 (1H, s), 6.66 (1H, s), 6.91 (2H, m), 7.3–8.1 (6H, m).

Next, the non-oxalate of the Compound 31 was treated with oxalic acid dihydrate in the same manner as in Example 2-(2) to obtain 1,3-dimethyl-6-(4-[2-(2-phenyl-4-oxo-4H-1-benzopyran-6-yl)oxyethyl]piperazine-1-yl)-2,4(1H,3H)-pyrimidinedione oxalate (Compound 31).

Analytical results of the obtained Compound 31:

Melting point: 140°–144° C. (decomposed)

Elemental analysis (as $C_{27}H_{28}N_4O_5 \cdot (COOH)_2 \cdot 3H_2O$). Calcd. (%): C 55.06; H 5.58; N 8.86. Found (%): C 54.92; H 5.41; N 8.69.

IR $\nu_{max}^{KBr}$ (cm$^{-1}$): 3400, 1710, 1630, 1600, 1440, 1250, 1190, 760, 710.

EXAMPLE 10

Preparation of 1,3-dimethyl-6-(2-[N-ethyl-N-[2-(2-ethoxycarbonyl-4-oxo-4H-1-benzopyran-7-yl)oxyethyl]-amino]ethylamino)-2,4(1H,3H)-pyrimidinedione oxalate (Compound 34):

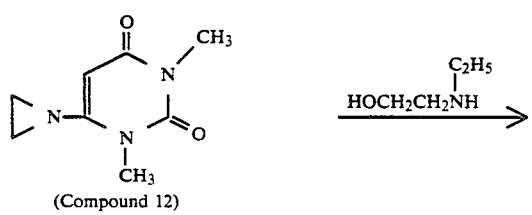

-continued

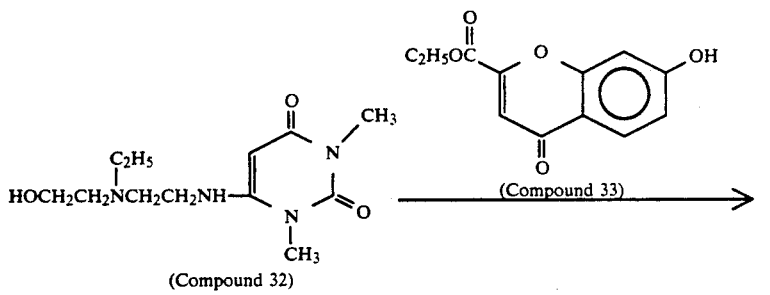
(Compound 32) → (Compound 33)

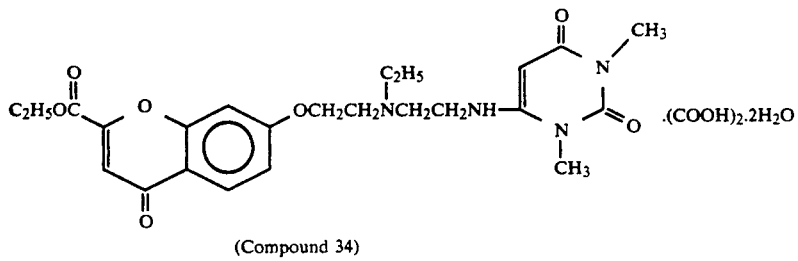
(Compound 34)

(1) Synthesis of N-ethyl-N-(2-hydroxyethyl)-N'-[1,3-dimethyl-2,4-dioxopyrimidine-6-yl]ethylenediamine (Compound 32):

In 100 ml of acetonitrile were dissolved 1.81 g of 6-(1-aziridinyl)-1,3-dimethyl-2,4(1H,3H)-pyrimidinedione (Compound 12), 1.07 ml of N-ethylaminoethanol and 50 mg of p-tolunesulfonic acid monohydrate, and the resultant solution was concentrated under reduced pressure. Afterward, the resultant residue was reacted at 80° C. for 3 hours, and chloroform was added to the resultant reaction mixture and the solution was then washed with water twice. After the washing, the formed chloroform layer was dried over anhydrous sodium sulfate in order to obtain 1.54 g (yield 58%) of oily N-ethyl-N-(2-hydroxyethyl)-N'-[1,3-dimethyl-2,4-dioxopyrimidine-6-yl]ethylenediamine (Compound 32).

Analytical results of the obtained Compound 32:

NMR (CDCl$_3$) δ ppm: 1.03 (3H, t), 2.4–3.2 (8H, m), 3.19 (3H, s), 3.34 (3H, s), 3.59 (2H, t), 4.01 (1H, br), 4.65 (1H, s), 6.31 (1H, br).

(2) Preparation of 1,3-dimethyl-6-(2-[N-ethyl-N-[2-(2-ethoxycarbonyl-4-oxo-4H-1-benzopyran-7-yl)oxyethyl]amino]ethylamino)-2,4(1H,3H)-pyrimidinedione oxalate (Compound 34):

The same procedure as in Example 8-(2) was effected so as to react and treat 0.6 g of N-ethyl-N-(2-hydroxyethyl)-N'[1,3-dimethyl-2,4-dioxopyrimidine-6-yl]ethylenediamine (Compound 32), 0.57 g of 2-ethoxycarbonyl-7-hydroxy-4-oxo-4H-1-benzopyran (Compound 33), 30 ml of tetrahydrofuran containing 0.77 g of triphenylphosphine and 0.47 ml of diethyl azodicarboxylate, thereby obtaining 0.81 g (yield 69%) of oily 1,3-dimethyl-6-(2-[N-ethyl-N-[2-(2-ethoxycarbonyl-4-oxo-4H-1-benzopyran-7-yl)oxyethyl]amino]ethylamino)-2,4(1H,3H)-pyrimidinedione (the non-oxalate of Compound 34).

Analytical results of the obtained non-oxalate of the Compound 34:

NMR (CDCl$_3$) δ ppm: 1.21 (3H, t), 1.33 (3H, t), 3.75 (2H, q), 2.8–3.7 (6H, m), 4.1–4.4 (4H, m), 3.50 (6H, s), 4.83 (1H, s), 5.74 (1H, br), 6.94 (2H, m), 7.31 (1H, s), 7.92 (1H, dd).

Next, the non-oxalate of the Compound 34 was treated with oxalic acid dihydrate in the same manner as in Example 2-(2) to obtain 1,3-dimethyl-6-(2-[N-ethyl-N-[2-(2-ethoxycarbonyl-4-oxo-4H-1-benzopyran-7-yl)oxyethyl]-amino]ethylamino)-2,4(1H,3H)-pyrimidinedione oxalate (Compound 34).

Analytical results of the obtained Compound 34:

Melting point: 138°–139° C. (decomposed).

Elemental analysis (as C$_{23}$H$_{30}$N$_4$O$_7$·(COOH)$_2$·½H$_2$O). Calcd. (%): C 52.35; H 5.80; N 9.77. Found (%): C 52.55; H 5.82; N 9.52.

IR $\nu_{max}^{KBr}$ (cm$^{-1}$): 3350, 2950, 1730, 1690, 1620, 1440, 1240, 1010, 780, 750, 720.

EXAMPLE 11

Preparation of 1,3-dimethyl-6-(4-[3-(2-phenyl-4-oxo-4H-1-benzopyran-5-yl)oxy-2-hydroxypropyl]piperazine-1-yl)-2,4(1H,3H)-pyrimidinedione hydrochloride (Compound 37):

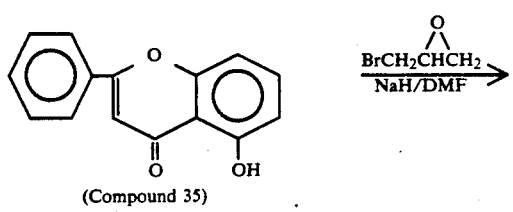
(Compound 35)

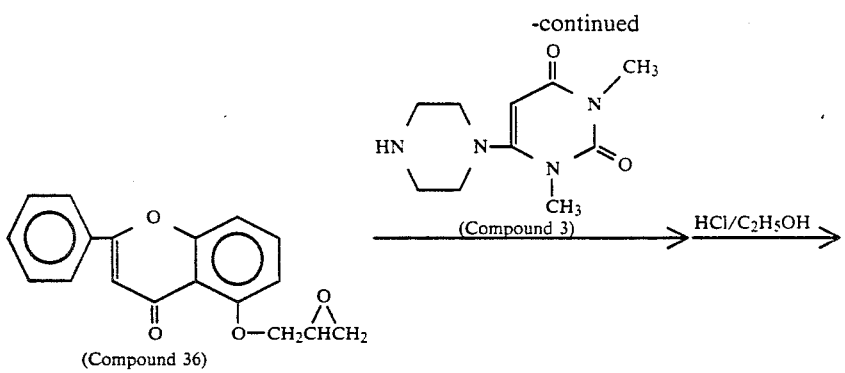

(1) Synthesis of 2-phenyl-5-(2,3-epoxypropoxy)-4-oxo-4H-1-benzopyran (Compound 36):

In 30 ml of dry N,N-dimethylformamide (DMF) were dissolved 1.67 g of 2-phenyl-5-hydroxy-4-oxo-4H-1-benzopyran (Compound 35), and 0.31 g of 60% sodium hydride was further added thereto, followed by stirring at 40° C. for 15 minutes. After completion of the stirring, 2.5 ml of epibromohydrin was added thereto, and reaction was carried out at 60° C. for 4 hours. Next, 3 ml of methanol and then 10 ml of water were added to the resultant reaction solution. The solution was then concentrated under reduced pressure, and 200 ml of chloroform and 100 ml of water were added to the resultant residue. After stirring and then liquid separation, the resultant chloroform layer was dried over anhydrous sodium sulfate, purified through a silica gel column chromatograph (chloroform:acetone=100:0 to 100:3 in volume ratio), and then crystallized from ethyl ether, thereby obtaining 1.56 g (yield 76%) of 2-phenyl-5-(2,3-epoxypropoxy)-4-oxo-4H-1-benzopyran (Compound 36) Melting point of the Compound 36: 126° to 128° C.

(2) Synthesis of 1,3-dimethyl-6-(4-[3-(2-phenyl-4-oxo-4H-1-benzopyran-5-yl)oxy-2-hydroxypropyl]piperazine-1-yl)-2,4(1H,3H)-pyrimidinedione hydrochloride (Compound 37):

In 30 ml of ethanol, there were heated under reflux for 3 hours 0.88 g of 2-phenyl-5-(2,3-epoxypropoxy)-4-oxo-4H-1-benzopyran (Compound 36) and 0.67 g of 1,3-dimethyl-6-(piperazine-1-yl)-2,4(1H,3H)-pyrimidinedione (Compound 3), and the reaction solution was then concentrated under reduced pressure. The resultant residue was purified through a silica gel column chromatograph (chloroform:methanol=100:1 to 100:5 in volume ratio), and then crystallized from ethyl acetate, thereby obtaining 1.21 g of 1,3-dimethyl-6-(4-[3-(2-phenyl-4-oxo-4H-1-benzopyran-5-yl)oxy-2-hydroxypropyl]piperazine-1-yl)-2,4(1H,3H)-pyrimidinedione (the non-hydrochloride of Compound 37).

Analytical results of the obtained non-hydrochloride of Compound 37:

Melting point: 126°-128° C.

NMR (CDCl$_3$) δ ppm: 2.1-2.5 (1H, m), 2.5-3.1 (10H, m), 3.31 (3H, s), 3.37 (3H, s), 4.0-4.4 (2H, m), 5.20 (1H, s), 6.66 (1H, s), 6.83 (1H, d), 7.13 (1H, d), 7.53 (1H, d), 7.3-8.0 (5H, m).

Next, the non-hydrochloride of Compound 37 was treated with HCl/C$_2$H$_5$OH in the same manner as in Example 1-(2) to obtain 1.2 g (Compound 37) of 1,3-dimethyl-6-(4-[3-(2-phenyl-4-oxo-4H-1-benzopyran-5-yl)oxy-2-hydroxypropyl]piperazine-1-yl)-2,4(1H,3H)-pyrimidinedione hydrochloride (Compound 37).

Analytical results of the obtained Compound 37:

Melting point: 109°-113° C. (decomposed)

Elemental analysis (as $C_{28}H_{30}N_4O_6 \cdot HCl \cdot 3.5H_2O$). Calcd. (%): C 54.41; H 6.20; N 9.06; Cl 5.74. Found (%): C 54.56; H 5.98; N 9.04; Cl 6.05.

IR $\nu_{max}^{KBr}$ (cm$^{-1}$): 3400, 1385, 1270, 1100, 795, 760

EXAMPLE 12

With regard to the compounds prepared by the same procedure as in Example 1 or Example 2, their names, structural formulae, starting materials substituted for Compound 1 or 5, melting points, and analytical results of IR and NMR of non-acid adducts will be described.

(1) 1,3-Dimethyl-6-(4-[3-(4-oxo-4H-1-benzopyran-5-yl)oxypropyl]pyperazine-1-yl)-2,4(1H,3H)-pyrimidinedione hydrochloride (Compound 38):

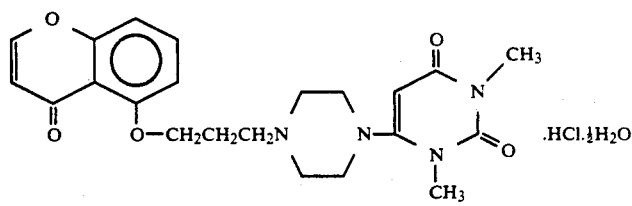
(Compound 38)

Starting material: 5-Hydroxy-4-oxo-4H-1-benzopyran.
Melting point: 260° C. or higher
NMR (CDCl₃) δ ppm: 1.8–2.2 (2H, m), 2.4–3.0 (10H, m), 3.23 (3H, s), 3.29 (3H, s), 4.06 (2H, t), 5.08 (1H, s), 6.03 (1H, d), 6.64 (1H, d), 6.82 (1H, d), 7.30 (1H, d), 7.4–7.6 (1H, d-d).
IR $\nu_{max}^{KBr}$ (cm⁻¹): b 3440, 1695, 1655, 1605, 1280, 1085, 980, 835, 790, 760.

(2) 1,3-Dimethyl-6-(4-[3-(2-phenyl-4-oxo-4H-1-benzopyran-5-yl)oxypropyl]piperazine-1-yl)-2,4(1H,3H)-pyrimidinedione oxalate (Compound 39):

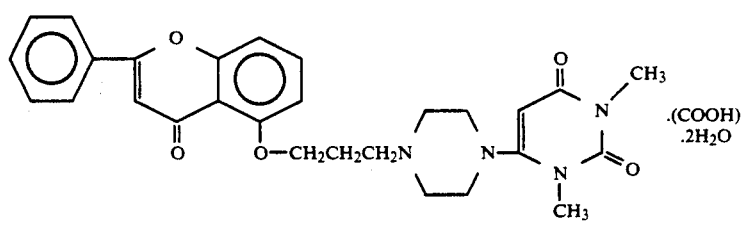
(Compound 39)

Starting material: 5-Hydroxy-2-phenyl-4-oxo-4H-1-benzopyran.
Melting point: 162° to 165° C. (decomposed).
NMR (CDCl₃) δ ppm: 1.9–2.3 (2H, m), 2.5–3.1 (10H, m), 3.28 (3H, s), 3.34 (3H, s), 4.13 (2H, t), 5.15 (1H, s), 6.6–7.9 (9H, m).
IR $\nu_{max}^{KBr}$ (cm⁻¹): 3400, 1690, 1600, 1385, 1265, 1095, 990, 795, 760, 600, 490.

(3) 1,3-Dimethyl-6-(4-[3-(2-methyl-4-oxo-4H-1-benzopyran-5-yl)oxypropyl-piperazine-1-yl)-2,4(1H,3H)-pyrimidinedione hydrochloride (Compound 40)

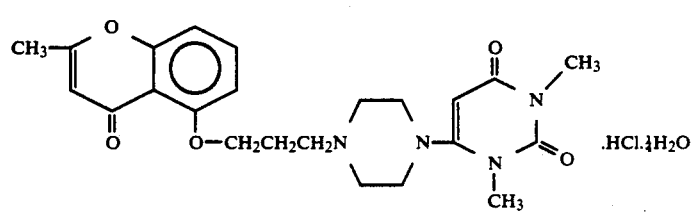
(Compound 40)

Starting material: 5-Hydroxy-2-methyl-4-oxo-4H-1-benzopyran.
Melting point: 250° C. or higher.
NMR (CDCl₃) δ ppm: 1.9–2.3 (2H, m), 2.33 (3H, s), 2.5–3.1 (j0H, m), 3.33 (3H, s), 3.40 (3H, s), 4.16 (2H, t), 5.30 (1H, s), 6.07 (1H, s), 6.7–7.7 (3H, m).
IR $\nu_{max}^{KBr}$ (cm⁻¹): 3400, 1700, 1430, 1385, 1315, 1255, 1200, 955, 830, 790, 750, 575.

(4) 1,3-Dimethyl-6-(4-[3-(2-phenyl-3-methyl-4-oxo-4H-1-benzopyran-5-yl)oxypropyl]pyperazine-1-yl)-2,4-(1H,3H)-pyrimidinedione oxalate (Compound 41):

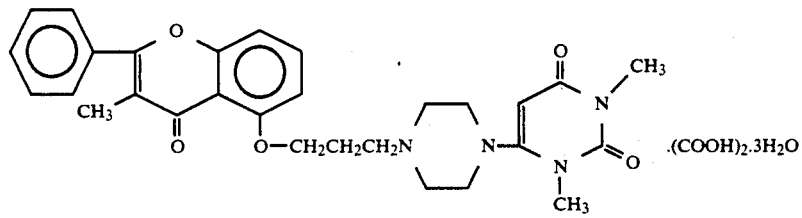
(Compound 41)

Starting material: 5-Hyroxy-3-methyl-2-phenyl-4-oxo-4H-1-benzopyran.
Melting point: 151° C. (decomposed).
NMR (CDCl₃) δ ppm: 2.1–3.1 (12H, m), 2.15 (3H, s), 3.34 (3H, s), 3.40 (3H, s), 4.20 (2H, t), 5.24 (1H, s), 4.18 (2H, t), 5.26 (1H, s), 6.12 (1H, s), 6.8–7.7 (8H, m).
IR $\nu_{max}^{KBr}$ (cm⁻¹): 3410, 1692, 1604, 1485, 1437, 1393, 1262, 1195.

(5) 1,3-Dimethyl-6-(4-[3-(3-phenyl-4-oxo-4H-1-benzopyran-5-yl)oxypropyl]pyperazine-1-yl)-2,4(1H,3H)-pyrimidinedione hydrochloride (Compound 42):

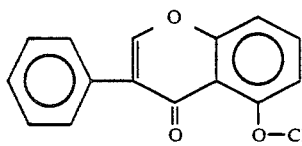
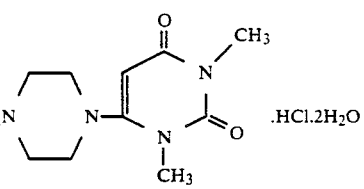

(Compound 42)

Starting material: 5-Hydroxy-3-phenyl-4-oxo-4H-1-benzopyran.
Melting point: 143° to 153° C.

(6) 1,3-Dimethyl-6-(4-[3-(2-ethoxycarbonyl-4-oxo4H-1-benzopyran-5-yl)oxypropyl]pyperazine-1-yl)-2,4-(1H,3H)-pyrimidinedione oxalate (Compound 43):

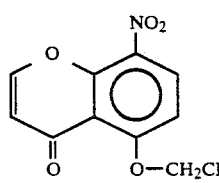

(Compound 43)

Starting material: 2-Ethoxycarbonyl-5-hydroxy-4-oxo-4H-1-benzopyran.
Melting point: 218° to 219° C. (decomposed).

NMR (CDCl₃) δ ppm: 1.43 (3H, t), 2.11 (2H, m), 2.77 (6H, m), 2.95 (4H, m), 3.29 (3H, s), 3.37 (3H, s), 4.11 (2H, t), 4.34 (2H, q), 5.22 (1H, s), 6.78 (3H, m), 7.31 (1H, m).
IR $\nu_{max}^{KBr}$ (cm$^{-1}$): 3400, 1700, 1650, 1620, 1440, 1230, 1080, 980, 800, 700.

(7) 1,3-Dimethyl-6-(4-[3-(8-nitro-4-oxo-4H-1-benzopyran-5-yl)oxypropyl]pyperazine-1-yl)-2,4(1H,3H)-pyrimidinedione oxalate (Compound 44):

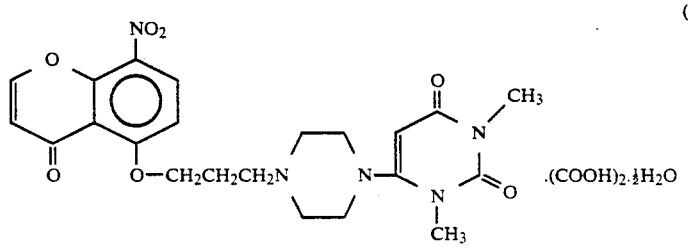

(Compound 44)

Starting material: 5-Hydroxy-8-nitro-4-oxo-4H-1-benzopyran.
Melting point: 165° to 167° C. (decomposed).
NMR (CDCl₃) δ ppm: 1.9-2.3 (2H, m), 2.5-3.1 (10H, m), 3.27 (3H, s), 3.36 (3H, s), 4.25 (2H, t), 5.16 (1H, s), 6.25 (1H, d), 6.81 (1H, d), 7.75 (1H, d), 8.24 (1H, d).
IR $\nu_{max}^{KBr}$ (cm$^{-1}$): 3400, 1650, 1600, 1520, 1305, 1270, 1080, 830, 755, 710.

(8) 1,3-Dimethyl-6-(4-[3-(6-nitro-4-oxo-4H-1-benzopyran-5-yl)oxypropyl]pyperazine-1-yl)-2,4(1H,3H)-pyrimidinedione oxalate (Compound 45):

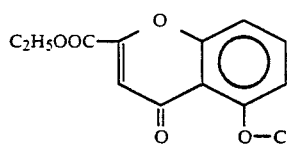
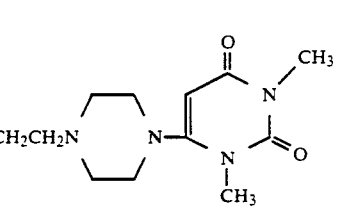

(Compound 45)

Starting material: 5-Hydroxy-6-nitro-4-oxo-4H-1-benzopyran.
Melting point: 160° to 165° C. (decomposed)
NMR (CDCl₃) δ ppm: 1 9-2.3 (2H, m), 4.26 (2H, t), 5.22 (1H, s), 6.28 (1H, d), 7.28 (1H, d), 7.78 (1H, d), 8.02 (1H, d).

NMR (CDCl₃) δ ppm: 1.9-2.3 (2H, m), 2.4-3.0 (10H, m), 3.34 (3H, s), 3.38 (3H, s), 4.20 (2H, t), 5.24 (1H, s), 6.85 (1H, d), 7.05 (1H, d), 7.2-7.7 (6H, m), 7.84 (1H, s).
IR $\nu_{max}^{KBr}$ (cm$^{-1}$): 3420, 1640, 1270, 1200, 1070, 820, 760, 700.

IR $\nu_{max}^{KBr}$ (cm$^{-1}$): 3400, 1650, 1600, 1520, 1340, 1115, 1015, 865,, 755, 700.

EXAMPLE 13

Preparation of 1,3-dimethyl-6-(2-[N-hydroxyethyl-N-[3(3-methyl-4-oxo-4H-1-benzopyran-5yl)oxypropyl-]amino]ethylamino)-2,4(1H,3H)-pyrimidinedione oxalate (Compound 46)

This compound was prepared by the same procedure as in Example 5 except that the Compound 16 in Example 5 was replaced with 3-(3-methyl-4-oxo-4H-1-benzopyran-5-yl)oxypropyl bromide. With regard to the Compound 46, its structural formula, melting point and analytical results of IR and NMR of non-acid adducts will be described.

Starting material: 5-Hydroxy-2-(pyridine-3-yl)-4-oxo-4H-1-benzopyran.

Melting point: 226° to 227° C. (decomposed).

NMR (CDCl$_3$) δ ppm: 1.07 (3H, t), 2.06 (2H, m), 2.58 (2H, q), 2.70 (2H, t), 2.93 (2H, t), 3.01 (3H, s), 3.03–3.07 (2H, m), 4.11 (2H, t), 4.55 (1H, s), 5.19 (1,H, b), 6.64 (1H, s), 6.50 (1H, d), 7.04 (1H, d), 7.44–7.56 (2H, m), 8.16–8.20 (1H, m), 8.73–8.76 (1H, m), 9.13 (1H, d).

IR $\nu_{max}^{KBr}$ (cm$^{-1}$): 3400, 3040, 1610, 1460, 1380, 1270, 1100, 790, 755, 675, 600.

EXAMPLE 15

With regard to compounds prepared by the same procedure as in Example 8-(1), reference will be made (Compound 46)

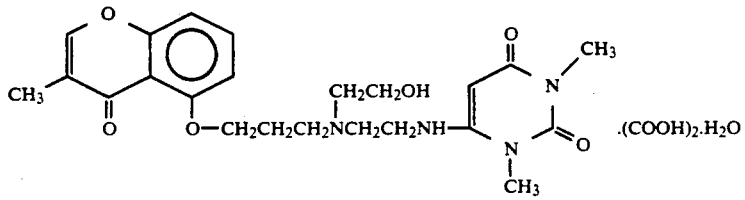

Melting point: 145° C. (decomposed).

NMR (CDCl$_3$) δ ppm: 1.97 (3H, s), 2.05 (2H, m), 2.67–2.77 (4H, m), 2.97–3.05 (4H, m), 3.03 (3H, s), 3.24 (3H, s), 3.72 (2H, m), 4.14 (2H, m), 4.46 (1H, s), 5.61 (1H, b), 6.68–7.42 (3H, m), 7.65 (2H,s).

IR $\nu_{max}^{KBr}$ (cm$^{-1}$): 3345, 3220, 3000, 1690, 1646, to their names, structural formulae, starting materials substituted for the Compound 27, melting points, and analytical results of IR and NMR of non-acid adducts.

(1) 1,3-Dimethyl-6-(4-[3-(2-phenyl-4-oxo-4H-1-benzopyran-7-yl)oxypropyl]piperazine-1-yl)-2,4(1H,3H)-pyrimidinedione oxalate (Compound 48)

(Compound 48)

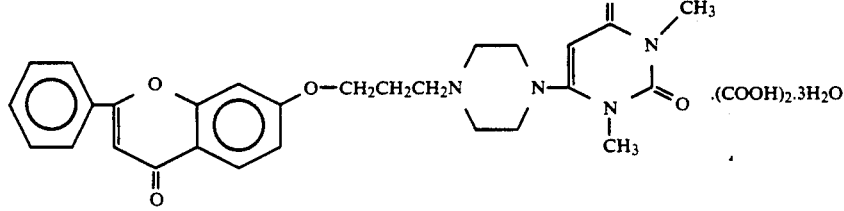

1608, 1543, 1469, 1166, 1090.

EXAMPLE 14

Preparation of 1,3-dimethyl-6-(4-[3-[2-(pyridine-3-yl)-4-oxo-4H-1-benzopyran-5-yl]oxypropyl]piperazine-1-yl)-2,4(1H,3H)-pyrimidinedione.2HCl.H$_2$O (Compound 47)

This compound was prepared by the same procedure as in Example 7. With regard to the Compound 47, its structural formula, starting material substituted for Compound 22, melting point and analytical results of IR and NMR of non-acid adducts will be described.

Starting material: 7-Hydroxy-2-phenyl-4-oxo-4H-1-benzopyran.

Melting point: 129° to 132° C. (decomposed).

NMR (CDCl$_3$) δ ppm: 2.05 (2H, m), 2.61 (6H, m), 2.98 (4H, m), 3.31 (3H, s), 3.38 (3H, s), 4.33 (2H, t), 5.26 (1H, s), 7.48 (6H, m), 8.07 (3H, m).

IR $\nu_{max}^{KBr}$ (cm$^{-1}$): 3350, 1700, 1620, 1440, 1380, 1170, 760, 710.

(2) 1,3-Dimethyl-6-(4-[3-(2-phenyl-4-oxo-4H-1-benzopyran-8-yl)oxypropyl]piperazine-1-yl)-2,4(1H,3H)-pyrimidinedione oxalate (Compound 49):

(Compound 47)

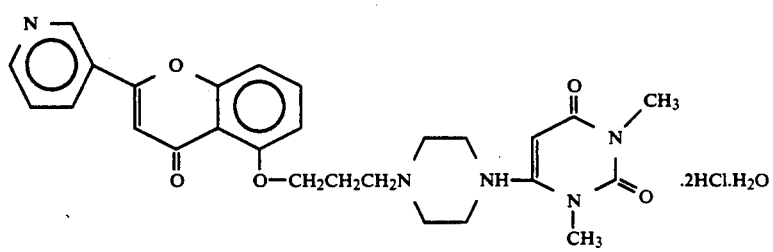

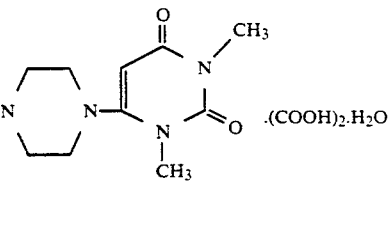

(Compound 49)

Starting material: 8-Hydroxy-2-phenyl-4H-1-benzopyran.

Melting point: 245° to 246° C. (decomposed).

NMR (CDCl₃) δ ppm: 2.0 (2H, m), 2.4–3.0 (10H, m), 3.33 (3H, s), 3.41 (3H, s), 4.25 (2H, m), 5.35 (1H, s), 7.3–8.1 (9H, m).

IR $\nu_{max}^{KBr}$ (cm⁻¹): 3400, 2550, 1700, 1630, 1610, 1440, 1380, 1240, 1090, 860, 760, 720.

(3) 1,3-Dimethyl-6-(4-[3-(2-ethoxycarbonyl-4-oxo-4H-1-benzopyran-7-yl)oxypropyl]piperazine-1-yl)-2,4-(1H,3H)-pyrimidinedione oxalate (Compound 50):

Starting material 2-Ethoxycarbonyl-6-hydroxy-4-oxo-4H-1-benzopyran.

Melting point: 137° to 139° C.

NMR (CDCl₃) δ ppm: 1.38 (3H, t), 2.09 (2H, m), 2.51–3.10 (10H, m), 3.30 (3H, s), 3.43 (3H, s), 4.07 (2H, t), 4.46 (2H, q), 5.20 (1H, s), 7.44 (2H, m), 8.01 (1H, m).

IR $\nu_{max}^{KBr}$ (cm⁻¹): 3400, 2600, 1740, 1700, 1650, 1440, 1250, 1080, 760, 720, 700.

(5) 1,3-Dimethyl-6-(4-[3-(2-phenyl-4-oxo-2,3-dihydro-4H-1-benzopyran-8-yl)oxypropyl]piperazine-1-yl)-2,4(1H,3H)-pyrimidinedione oxalate (Compound 52):

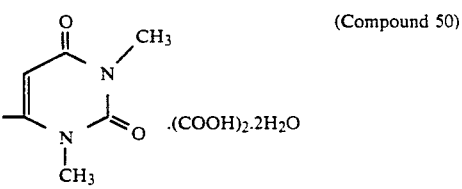

(Compound 50)

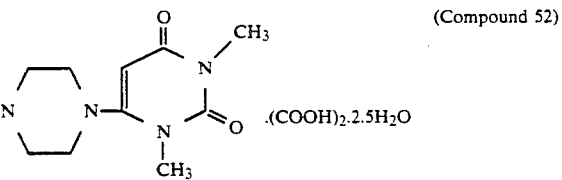

(Compound 52)

Starting material: 2-Ethoxycarbonyl-7-hydroxy-4-oxo-4H-1-benzopyran.

Melting point: 152° to 154° C. (decomposed).

NMR (CDCl₃) δ ppm: 1.53 (3H, t), 2.11 (2H, m), 2.64 (6H, m), 3.00 (4H, m), 3.32 (3H, s), 3.39 (3H, s), 4.18 (2H, t), 4.57 (2H, q), 5.27 (1H, s), 7.08 (3H, m), 8.08 (1H, m).

IR $\nu_{max}^{KBr}$ (cm⁻¹): 3400, 2550, 1740, 1700, 1640, 1440, 1250, 810, 720.

(4) 1,3-Dimethyl-6-(4-[3-(2-ethoxycarbonyl-4-oxo-4H-1-benzopyran-6-yl)oxypropyl]piperazine-1-yl)-2,4-(1H,3H)-pyrimidinedione oxalate (Compound 51):

Starting material: 8-Hydroxy-2-phenyl-4-oxo-2,3-dihydro-4H-1-benzopyran.

Melting point: 133° to 136° C. (decomposed).

NMR (CDCl₃) δ ppm: 2.0 (4H, m), 2.5–3.1 (10H, m), 3.31 (3H, s), 3.35 (3H, s), 4.03 (2H, b-t), 5.22 (1H, s), 6.8–7.5 (8H, m).

IR $\nu_{max}^{KBr}$ (cm⁻¹): 3400, 3010, 1760, 1700, 1650, 1490, 1200, 1150, 900, 840, 790, 760.

EXAMPLE 16

With regard to compounds prepared by the same procedure as in Example 4, reference will be made to their names, structural formulae and analytical results.

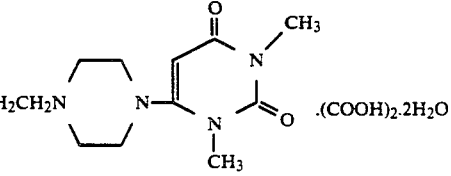

(Compound 51)

(1) 1,3-Dimethyl-6-(2-[N-ethyl-N-[3-(2-phenyl-4-oxo-4H-1-benzopyran-5-yl)oxypropyl]amino]ethylamino)-2,4(1H,3H)-pyrimidinedione oxalate (Compound 53):

This compound was prepared by the same procedure as in Example 4 except that the Compound 2 in Example 4 was replaced with 3-(2-phenyl-4-oxo-4H-1-benzopyran-5-yl)oxypropyl bromide.

opyrimidine-6-yl)-N'-ethylethylenediamine (Compound 13). Reference will be made to the structural formula and melting point of the Compound 55, and analytical results of IR and NMR of non-acid adducts.

(Compound 55)

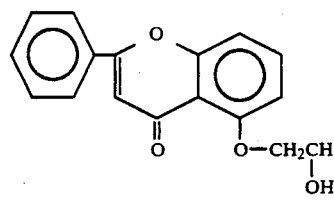
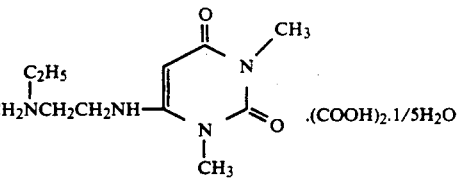

Melting point: 226° to 227° C. (decomposed).
NMR (CDCl$_3$) δ ppm: 1.04 (3H, t), 2.62–2.85 (5H, m), 2.91–3.02 (H, m), 3.09–3.14 (2H, m), 3.22 (3H, s), 3.38

(Compound 53)

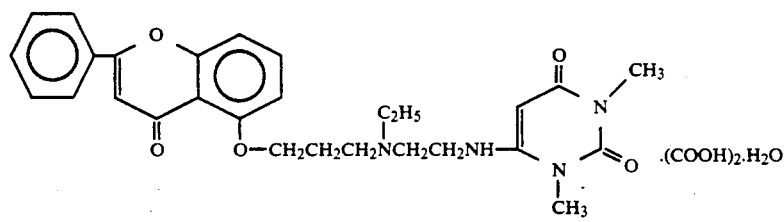

Melting point: 244° C. (decomposed).
Elemental analysis (as C$_{28}$H$_{32}$N$_4$O$_5$.(COOH)$_2$.H$_2$O). Calcd. (%): C 57.99; H 6.04; N 9.33. Found (%): C 54.78; H 5.75; N 9.46.

IR $\nu_{max}^{KBr}$ (cm$^{-1}$): 3240, 2980, 1700, 1630, 1530, 1642, 1390, 1090, 1030, 775, 750, 690, 670.

(2) 1,3-Dimethyl-6-(2-[N-ethyl-N-[3-(3-methyl-2-phenyl-4-oxo-4H-1-benzopyran-5-yl)oxypropyl]amino]ethyl-amino)-2,4(1H,3H)-pyrimidinedione oxalate (Compound 54):

This compound was prepared by the same procedure as in Example 4 except that the Compound 2 in Example 4 was replaced with 3-(3-methyl-2-phenyl-4-oxo-4H-1-benzopyran-5-yl)oxypropyl bromide.

(3H, s), 4.00 (1H, d-d), 4.15 (1H, m), 4.30 (1H, d-d), 4.79 (1H, s), 6.29 (1H, b), 6.71 (1H, s), 6.90 (1H, d), 7.22 (1H, d), 7.27 (1H, s), 7.51–7.63 (3H, m).

IR $\nu_{max}^{KBr}$ (cm$^{-1}$): 3400, 3050, 1605, 1550, 1460, 1380, 1270, 1100, 1040, 860, 760, 605.

EXAMPLE 18

Production of tablets containing, as an effective ingredient, 1,3-dimethyl-6-(4-[3-(2-methyl-4-oxo-4H-1-benzopyran-5-yl)oxypropyl]piperazine-1-yl)-2,4(1H,3H)-pyrimidinedione hydrochloride (Compound 40) which can be obtained by the procedure of Example 12-(3):

With 20 g of corn starch were mixed 1 g of the above (Compound 54)

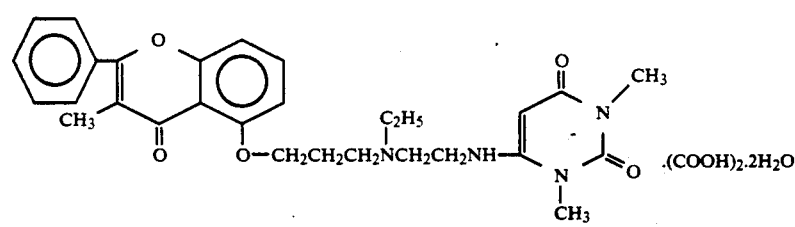

Melting point: 145° C. (decomposed).
Elemental analysis (as C$_{29}$H$_{34}$N$_4$O$_5$.(COOH)$_2$.2H$_2$O): Calcd. (%): C 57.76; H 6.25; N 8.69. Found (%): C 58.00; H 6.32; N 8.57.

IR $\nu_{max}^{KBr}$ (cm$^{-1}$): 3410, 3240, 2850, 1690, 1605, 1460, 1180, 700, 680, 490.

EXAMPLE 17

1,3-Dimethyl-6-(2-[N-ethyl-N-[3-(2-phenyl-4-oxo-4H-1-benzopyran-5-yl)oxy-2-hydroxypropyl]amino]ethylamino)-2,4(1H,3H)-pyrimidinedione oxalate (Compound 55):

This compound was prepared by the same procedure as in Example 11 except that the Compound 3 in Example 11 was replaced with N-(1,3-dimethyl-2,4-dioxpyrimidinedione derivative hydrochloride (Compound 40) and 123 g of lactose, and the mixture was further mixed with a solution prepared by dissolving 5 g of hydroxypropyl cellulose in 100 ml of water, so as to form grains, followed by drying the grains at 50° C. for 4 hours. Afterward, 1 g of magnesium stearate was added to the dried grains and then mixed sufficiently. The mixture was then formed into tablets by the use of a tableting machine, the weight of each tablet being 150 mg.

EXAMPLE 19

Preparation of capsules containing, as an effective component, 1,3-dimethyl-6-(4-[3-(4-oxo-4H-1-benzopyran-5-yl)oxypropyl]piperazine-1-yl)-2,4(1H,3H)-pyrimidine-dione hydrochloride (Compound 38) which can be obtained by the procedure of Example 12-(1):

With 25 g of corn starch were sufficiently mixed 5 g of the above pyrimidinedione derivative hydrochloride (Compound 38) and 120 g of lactose, and hard capsules were filled with the resultant mixture by the use of a capsule filling machine to obtain capsules, the content of the mixture in each capsule being 150 mg.

EXAMPLE 20

Preparation of an injection containing, as an effective component, 1,3-dimethyl-6-(4-[3-(3-methyl-4-oxo-4H-1-benzopyran-5-yl)oxypropyl]piperazine-1-yl)-2,4(1H,3H)-pyrimidinedione hydrochloride (Compound 4) which can be obtained by the procedure of Example 1:

In distilled water for injection were dissolved 20 mg of the above pyrimidinedione derivative oxalate (Compound 4) and 0.85 g of sodium chloride, and the total volume of the liquid was then regulated to be 100 ml, thereby preparing an injection.

Pharmacological Test (1) Influence on myocardial action potential duration time ($APD_{75}$):

To a hybrid adult dog, 30 mg/kg of pentobarbital was administered through a vein, and after being anesthetized, the heart was removed. Afterward, the right ventricular free wall of the heart was cut and taken out in a Tyrode solution.

The right ventricular free wall was fixed in an incubator at 37° C., and a nutritional solution (20 ml of the Tyrode solution) was refluxed.

In this isolated condition, myocardial action potential duration times ($APD_{75}$) were measured before and after the administration of the respective compounds prepared in the above examples in Table 1 and d-sotalol as a control medicine, and $APD_{75}(\%)$ was calculated from the measured results in accordance with the formula:

$$APD_{75}(\%) = (B-A)/A \times 100$$

A: $APD_{75}$ before administration
B: $APD_{75}$ after administration

Here, $APD_{75}$ was measured as follows: A field stimulation of 1 Hz was given to the right ventricular free wall, and any variation of an action potential was depicted on an oscilloscope via a glass microelectrode (10 to 20 MΩ) thrust into a Purkinje fiber of the free wall and via an amplifier. Afterward, a waveform on the oscilloscope was analyzed by the use of a computer, and the time of from a point of the action potential generation to a point of 75% repolarization was measured. This measured time was regarded as the myocardial action potential duration time ($APD_{75}$).

Each of the compounds shown in Table 1 was separately added to the refluxing nutritional solution (20 ml), and after 20 minutes' incubation, $APD_{75}$ after the administration was calculated from the variation of the myocardial action potential duration time.

Incidentally, this test was carried out in accordance with a Sato et al's method [H. Sato, K. Hashimoto, Arzneimeittel Forschung, 34 (1), 3a, 376–380 (1984)].

The results are set forth in Table 1.

(2) Influence on ventricular muscle refractory period:

Refractory periods were measured in the following manner before and after each of the compounds and d-sotalol shown in Table 1 was separately administered to a vein or a duodenum, and ERP (%; extensibility of refractory period) was calculated from the measured values in accordance with the following formula:

$$ERP(\%) = (W-Y)/Y \times 100$$

W: Refractory period after administration
Y: Refractory period before administration To a mongrel adult dog, 30 mg/kg of pentobarbital was administered intravenously, and after being anesthetized, a pair of silver-silver chloride electrodes separated by 3 mm was sewn on an opened right ventricule, and electrical stimulation was given at an interval of 400 msec at a duration time of 4 msec under a current twice as much as the threshold. Afterward, a small amount of alcohol was injected into a sinus artery in order to extinguish a pacemaker activity, and the ventricular refractory period (ERP) was measured under ventricule pacing.

That is, 1 train comprised 10 stimulations, and an interval between two of the trains was usually 400 msec. At the time of the refractory period measurement, however, the above interval was shortened every 10 smec, and the interval between the trains at the time when reaction to the first stimulation of the train disappeared was regarded as the refractory period.

In this case, the electrical stimulation was fed in accordance with a program by a heart stimulation device (Diamedical Co., Ltd.; DHM-226-3).

The results are set forth in Table 1.

Toxicity Test

Each of the compounds prepared in the above-mentioned examples shown in Table 2 was administered into a mouse (ddy strain, male). In each case, the administration was effected by oral administration (p.o.) in a dose of 300 mg/kg.

A mortality rate (number of specimens: one group = 2 to 4 mice) of the mice 24 hours after the administration was calculated, and the results are set forth in Table 2.

TABLE 1

| | (results of pharmacological test) | | | | | | | |
|---|---|---|---|---|---|---|---|---|
| Compound | $APD_{75}$ (%) Dose (μg/ml) | | | | ERP (%) Dose (mg/kg, i.v.) | | | |
| No. | 0.3 | 1.0 | 3.0 | 10.0 | 0.1 | 0.3 | 1.0 | 3.0 |
| 4 | — | 24 | 30 | — | 6.3 | 12.5 | 12.5 | 25.0 |
| 7 | — | 25 | 31 | — | 12 | 18 | 18 | 24 |
| 14 | — | 4 | 17 | 25 | 6.8 | 6.8 | 10.7 | 13.6 |
| 21 | — | 12 | 16 | 20 | 0 | 0 | 0 | 7.7 |
| 25 | — | 7 | 19 | 27 | 6.3 | 6.7 | 12.5 | — |
| 38 | — | 10 | 20 | 39 | 4.5 | 9.3 | 16.0 | 16.0 |
| 39 | — | 7 | 20 | — | 7.1 | 14.3 | 14.3 | 14.3 |
| 40 | — | 18 | 25 | 29 | 6.9 | 10.3 | 13.9 | 17.4 |
| 48 | — | 7 | 12 | — | 0 | 0 | 6.9 | 20.4 |
| 50 | — | 7 | 14 | 28 | 0 | 0 | 0 | 6.3 |
| d-sotalol | 0 | 3 | 7.4 | 15.8 | 1.7 | 6.7 | 8.7 | 15.5 |

TABLE 2

(results of toxicity test)

| Compound Number | Mortality Rate (%) |
| --- | --- |
| 4 | 0 |
| 7 | 0 |
| 14 | 0 |
| 21 | 0 |
| 25 | 0 |
| 38 | 0 |
| 39 | 0 |
| 40 | 0 |

What is claimed is:

1. A pyrimidinedione compound of the formula

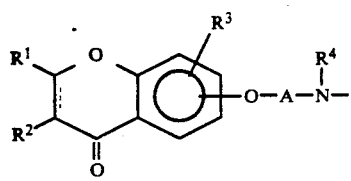

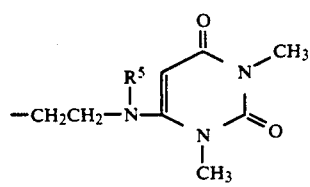

wherein A is —(CH$_2$)$_n$—, n is 2 or 3 or —CH$_2$CH(OH)CH$_2$—, and R$^1$ is hydrogen, a lower alkyl group, lower alkoxycarbonyl group, phenyl group, 4-pyridyl group, 3-pyridyl group or 2-pyridyl group, R$^2$ is hydrogen, a lower alkyl group or phenyl group, R$^3$ is hydrogen or a nitro group, $=$ is a single bond or double bond, R$^4$ is a lower alkyl group or a lower alkyl group substituted by a hydroxyl group, and R$^5$ is hydrogen or may be combined with R$^4$ to form —CH$_2$CH$_2$— or a pharmaceutically acceptable salt thereof.

2. The compound according to claim 1 wherein R$^3$ is present at the 6-position or 8-position of the 1-benzopyran ring in said formula.

3. The compound according to claim 1 wherein the following substituent

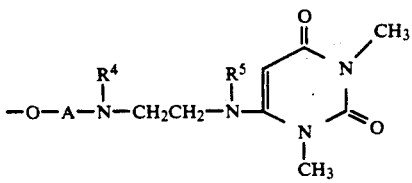

wherein A, R$^4$, and R$^5$ are defined as in claim 10, is present at the 5-position or 6-position of the 1-benzopyran ring in said formula.

4. An antiarrhythmic pharmaceutical composition comprising an antiarrhythmic effective amount of the compound of claim 1 or its pharmaceutically acceptable salt in admixture with an inert carrier.

5. A method of treating cardiac arrhythmias comprising administering to a person in need of same an effective amount of the compound of claim 1 or its pharmaceutically acceptable salt.

* * * * *